(12) United States Patent
Waycuilis et al.

(10) Patent No.: US 8,198,495 B2
(45) Date of Patent: Jun. 12, 2012

(54) PROCESSES AND SYSTEMS FOR THE STAGED SYNTHESIS OF ALKYL BROMIDES

(75) Inventors: John J. Waycuilis, Cypress, TX (US); William J. Turner, Seabrook, TX (US)

(73) Assignee: Marathon GTF Technology, Ltd., Houston, TX (US)

( * ) Notice: Subject to any disclaimer, the term of this patent is extended or adjusted under 35 U.S.C. 154(b) by 0 days.

(21) Appl. No.: 12/715,526

(22) Filed: Mar. 2, 2010

(65) Prior Publication Data
US 2011/0218372 A1 Sep. 8, 2011

(51) Int. Cl.
*C07C 1/00* (2006.01)
(52) U.S. Cl. ........ 585/408; 585/359; 585/469; 585/642; 585/733; 585/422
(58) Field of Classification Search .................. None
See application file for complete search history.

(56) References Cited

U.S. PATENT DOCUMENTS

| | | | |
|---|---|---|---|
| 2,168,260 A | 8/1939 | Heisel et al. | |
| 2,246,082 A | 6/1941 | Vaughan et al. | |
| 2,488,083 A | 11/1949 | Gorin et al. | |
| 2,536,457 A | 1/1951 | Mugdan | |
| 2,677,598 A | 5/1954 | Crummett et al. | |
| 2,941,014 A | 6/1960 | Rothweiler et al. | |
| 3,076,784 A | 2/1963 | Schulte-Huemann et al. | |
| 3,172,915 A | 3/1965 | Borkowski et al. | |
| 3,246,043 A | 4/1966 | Rosset et al. | |
| 3,254,023 A | 5/1966 | Miale et al. | |
| 3,273,964 A | 9/1966 | Rosset | |
| 3,291,708 A | 12/1966 | Juda | |
| 3,294,846 A | 12/1966 | Livak et al. | |
| 3,310,380 A | 3/1967 | Lester | |
| 3,346,340 A | 10/1967 | Louvar et al. | |
| 3,353,916 A | 11/1967 | Lester | |
| 3,353,919 A | 11/1967 | Stockman | |
| 3,379,506 A | 4/1968 | Massonne et al. | |
| 3,496,242 A | 2/1970 | Berkowitz et al. | |
| 3,562,321 A | 2/1971 | Borkowski et al. | |
| 3,598,876 A | 8/1971 | Bloch | |
| 3,657,367 A | 4/1972 | Blake et al. | |
| 3,670,037 A | 6/1972 | Dugan | |
| 3,673,264 A | 6/1972 | Kuhn | |
| 3,679,758 A | 7/1972 | Schneider | |
| 3,702,886 A | 11/1972 | Argauer et al. | |

(Continued)

FOREIGN PATENT DOCUMENTS

CA   1099656   4/1981

(Continued)

OTHER PUBLICATIONS

U.S. Appl. No. 60/487,364, filed Jul. 15, 2003, Lorkovic et al.

(Continued)

*Primary Examiner* — Tam M Nguyen
(74) *Attorney, Agent, or Firm* — Jack E. Ebel

(57) ABSTRACT

Processes and systems for synthesizing alkyl bromides to hydrocarbon products, such as high molecular weight hydrocarbons, olefins or mixtures thereof, wherein one or more streams of alkyl bromides may be synthesized in sequential or concurrent stages at different temperatures. The catalyst used in the synthesis stages may be the same or different and at least in one instance is chosen to form hydrocarbon products having a significant $C_{6+}$ paraffin content. The stages may be conducted in one or more reactors and the catalyst may be deployed in fixed beds or fluidized beds.

19 Claims, 5 Drawing Sheets

U.S. PATENT DOCUMENTS

| | | |
|---|---|---|
| 3,705,196 A | 12/1972 | Turner |
| 3,799,997 A | 3/1974 | Schmerling |
| 3,865,886 A | 2/1975 | Schindler et al. |
| 3,876,715 A | 4/1975 | McNulty et al. |
| 3,879,473 A | 4/1975 | Stapp |
| 3,879,480 A | 4/1975 | Riegel et al. |
| 3,883,651 A | 5/1975 | Woitun et al. |
| 3,886,287 A | 5/1975 | Kobayashi et al. |
| 3,894,103 A | 7/1975 | Chang et al. |
| 3,894,104 A | 7/1975 | Chang et al. |
| 3,894,105 A | 7/1975 | Chang et al. |
| 3,894,107 A | 7/1975 | Butter et al. |
| 3,907,917 A | 9/1975 | Forth |
| 3,919,336 A | 11/1975 | Kurtz |
| 3,920,764 A | 11/1975 | Riegel et al. |
| 3,923,913 A | 12/1975 | Antonini et al. |
| 3,928,483 A | 12/1975 | Chang et al. |
| 3,965,205 A | 6/1976 | Garwood et al. |
| 3,974,062 A | 8/1976 | Owen et al. |
| 3,987,119 A | 10/1976 | Kurtz et al. |
| 3,992,466 A | 11/1976 | Plank et al. |
| 4,006,169 A | 2/1977 | Anderson et al. |
| 4,011,278 A | 3/1977 | Plank et al. |
| 4,025,571 A | 5/1977 | Lago |
| 4,025,572 A | 5/1977 | Lago |
| 4,025,575 A | 5/1977 | Chang et al. |
| 4,025,576 A | 5/1977 | Chang et al. |
| 4,035,285 A | 7/1977 | Owen et al. |
| 4,035,430 A | 7/1977 | Dwyer et al. |
| 4,039,600 A | 8/1977 | Chang |
| 4,044,061 A | 8/1977 | Chang et al. |
| 4,046,825 A | 9/1977 | Owen et al. |
| 4,049,734 A | 9/1977 | Garwood et al. |
| 4,052,471 A | 10/1977 | Pearsall |
| 4,052,472 A | 10/1977 | Givens et al. |
| 4,058,576 A | 11/1977 | Chang et al. |
| 4,060,568 A | 11/1977 | Rodewald |
| 4,071,753 A | 1/1978 | Fulenwider et al. |
| 4,072,733 A | 2/1978 | Hargis et al. |
| 4,087,475 A | 5/1978 | Jordan |
| 4,088,706 A | 5/1978 | Kaeding |
| 4,092,368 A | 5/1978 | Smith |
| 4,105,755 A | 8/1978 | Darnell et al. |
| 4,110,180 A | 8/1978 | Nidola et al. |
| 4,117,251 A | 9/1978 | Kaufhold et al. |
| 4,129,604 A | 12/1978 | Tsao |
| 4,133,838 A | 1/1979 | Pearson |
| 4,133,966 A | 1/1979 | Pretzer et al. |
| 4,138,440 A | 2/1979 | Chang et al. |
| 4,143,084 A | 3/1979 | Kaeding et al. |
| 4,156,698 A | 5/1979 | Dwyer et al. |
| 4,169,862 A | 10/1979 | Eden |
| 4,172,099 A | 10/1979 | Severino |
| 4,187,255 A | 2/1980 | Dodd |
| 4,191,618 A | 3/1980 | Coker et al. |
| 4,194,990 A | 3/1980 | Pieters et al. |
| 4,197,420 A | 4/1980 | Ferraris et al. |
| 4,219,680 A | 8/1980 | Konig et al. |
| 4,249,031 A | 2/1981 | Drent et al. |
| 4,252,687 A | 2/1981 | Dale et al. |
| 4,270,929 A | 6/1981 | Dang Vu et al. |
| 4,272,338 A | 6/1981 | Lynch et al. |
| 4,282,159 A | 8/1981 | Davidson et al. |
| 4,300,005 A | 11/1981 | Li |
| 4,300,009 A | 11/1981 | Haag et al. |
| 4,301,253 A | 11/1981 | Warren |
| 4,302,619 A | 11/1981 | Gross et al. |
| 4,307,261 A | 12/1981 | Beard, Jr. et al. |
| 4,308,403 A | 12/1981 | Knifton |
| 4,311,865 A | 1/1982 | Chen et al. |
| 4,317,800 A | 3/1982 | Sloterdijk et al. |
| 4,317,934 A | 3/1982 | Seemuth |
| 4,317,943 A | 3/1982 | Knifton |
| 4,320,241 A | 3/1982 | Frankiewicz |
| 4,333,852 A | 6/1982 | Warren |
| 4,347,391 A | 8/1982 | Campbell |
| 4,350,511 A | 9/1982 | Holmes et al. |
| 4,356,159 A | 10/1982 | Norval et al. |
| 4,371,716 A | 2/1983 | Paxson et al. |
| 4,373,109 A | 2/1983 | Olah |
| 4,376,019 A | 3/1983 | Gamlen et al. |
| 4,380,682 A | 4/1983 | Leitert et al. |
| 4,384,159 A | 5/1983 | Diesen |
| 4,389,391 A | 6/1983 | Dunn, Jr. |
| 4,410,714 A | 10/1983 | Apanel |
| 4,412,086 A | 10/1983 | Beard, Jr. et al. |
| 4,418,236 A | 11/1983 | Cornelius et al. |
| 4,431,856 A | 2/1984 | Daviduk et al. |
| 4,433,189 A | 2/1984 | Young |
| 4,433,192 A | 2/1984 | Olah |
| 4,439,409 A | 3/1984 | Puppe et al. |
| 4,440,871 A | 4/1984 | Lok et al. |
| 4,443,620 A | 4/1984 | Gelbein et al. |
| 4,462,814 A | 7/1984 | Holmes et al. |
| 4,465,884 A | 8/1984 | Degnan et al. |
| 4,465,893 A | 8/1984 | Olah |
| 4,467,130 A | 8/1984 | Olah |
| 4,467,133 A | 8/1984 | Chang et al. |
| 4,489,210 A | 12/1984 | Judat et al. |
| 4,489,211 A | 12/1984 | Ogura et al. |
| 4,492,657 A | 1/1985 | Heiss |
| 4,496,752 A | 1/1985 | Gelbein et al. |
| 4,497,967 A | 2/1985 | Wan |
| 4,499,314 A | 2/1985 | Seddon et al. |
| 4,506,105 A | 3/1985 | Kaufhold |
| 4,509,955 A | 4/1985 | Hayashi |
| 4,513,092 A | 4/1985 | Chu et al. |
| 4,513,164 A | 4/1985 | Olah |
| 4,523,040 A | 6/1985 | Olah |
| 4,524,227 A | 6/1985 | Fowles et al. |
| 4,524,228 A | 6/1985 | Fowles et al. |
| 4,524,231 A | 6/1985 | Fowles et al. |
| 4,538,014 A | 8/1985 | Miale et al. |
| 4,538,015 A | 8/1985 | Miale et al. |
| 4,540,826 A | 9/1985 | Banasiak et al. |
| 4,543,434 A | 9/1985 | Chang |
| 4,544,781 A | 10/1985 | Chao et al. |
| 4,547,612 A | 10/1985 | Tabak |
| 4,550,217 A | 10/1985 | Graziani et al. |
| 4,550,218 A | 10/1985 | Chu |
| 4,568,660 A | 2/1986 | Klosiewicz |
| 4,579,977 A | 4/1986 | Drake |
| 4,579,992 A | 4/1986 | Kaufhold et al. |
| 4,579,996 A | 4/1986 | Font Freide et al. |
| 4,587,375 A | 5/1986 | Debras et al. |
| 4,588,835 A | 5/1986 | Torii et al. |
| 4,590,310 A | 5/1986 | Townsend et al. |
| 4,599,474 A | 7/1986 | Devries et al. |
| 4,605,796 A | 8/1986 | Isogai et al. |
| 4,605,803 A | 8/1986 | Chang et al. |
| 4,621,161 A | 11/1986 | Shihabi |
| 4,621,164 A | 11/1986 | Chang et al. |
| 4,633,027 A | 12/1986 | Owen et al. |
| 4,634,800 A | 1/1987 | Withers, Jr. et al. |
| 4,642,403 A | 2/1987 | Hyde et al. |
| 4,642,404 A | 2/1987 | Shihabi |
| 4,652,688 A | 3/1987 | Brophy et al. |
| 4,654,449 A | 3/1987 | Chang et al. |
| 4,655,893 A | 4/1987 | Beale |
| 4,658,073 A | 4/1987 | Tabak |
| 4,658,077 A | 4/1987 | Kolts et al. |
| 4,665,259 A | 5/1987 | Brazdil et al. |
| 4,665,267 A | 5/1987 | Barri |
| 4,665,270 A | 5/1987 | Brophy et al. |
| 4,675,410 A | 6/1987 | Feitler et al. |
| 4,690,903 A | 9/1987 | Chen et al. |
| 4,695,663 A | 9/1987 | Hall et al. |
| 4,696,985 A | 9/1987 | Martin |
| 4,704,488 A | 11/1987 | Devries et al. |
| 4,704,493 A | 11/1987 | Devries et al. |
| 4,709,108 A | 11/1987 | Devries et al. |
| 4,720,600 A | 1/1988 | Beech, Jr. et al. |
| 4,720,602 A | 1/1988 | Chu |
| 4,724,275 A | 2/1988 | Hinnenkamp et al. |
| 4,735,747 A | 4/1988 | Ollivier et al. |
| 4,737,594 A | 4/1988 | Olah |
| 4,748,013 A | 5/1988 | Saito et al. |

| | | | | | |
|---|---|---|---|---|---|
| 4,762,596 A | 8/1988 | Huang et al. | 5,097,083 A | 3/1992 | Stauffer |
| 4,769,504 A | 9/1988 | Noceti et al. | 5,099,084 A | 3/1992 | Stauffer |
| 4,774,216 A | 9/1988 | Kolts et al. | 5,105,045 A | 4/1992 | Kimble et al. |
| 4,775,462 A | 10/1988 | Imai et al. | 5,105,046 A | 4/1992 | Washecheck |
| 4,777,321 A | 10/1988 | Harandi et al. | 5,107,032 A | 4/1992 | Erb et al. |
| 4,781,733 A | 11/1988 | Babcock et al. | 5,107,051 A | 4/1992 | Pannell |
| 4,783,566 A | 11/1988 | Kocal et al. | 5,107,061 A | 4/1992 | Ou et al. |
| 4,788,369 A | 11/1988 | Marsh et al. | 5,108,579 A | 4/1992 | Casci |
| 4,788,377 A | 11/1988 | Chang et al. | 5,118,899 A | 6/1992 | Kimble et al. |
| 4,792,642 A | 12/1988 | Rule et al. | 5,120,332 A | 6/1992 | Wells |
| 4,795,732 A | 1/1989 | Barri | 5,132,343 A | 7/1992 | Zwecker et al. |
| 4,795,737 A | 1/1989 | Rule et al. | 5,138,112 A | 8/1992 | Gosling et al. |
| 4,795,843 A | 1/1989 | Imai et al. | 5,139,991 A | 8/1992 | Taylor et al. |
| 4,795,848 A | 1/1989 | Teller et al. | 5,146,027 A | 9/1992 | Gaffney |
| 4,804,797 A | 2/1989 | Minet et al. | 5,157,189 A | 10/1992 | Karra |
| 4,804,800 A | 2/1989 | Bortinger et al. | 5,160,502 A | 11/1992 | Kimble et al. |
| 4,808,763 A | 2/1989 | Shum | 5,166,452 A | 11/1992 | Gradl et al. |
| 4,814,527 A | 3/1989 | Diesen | 5,175,382 A | 12/1992 | Hebgen et al. |
| 4,814,532 A | 3/1989 | Yoshida et al. | 5,178,748 A | 1/1993 | Casci et al. |
| 4,814,535 A | 3/1989 | Yurchak | 5,185,479 A | 2/1993 | Stauffer |
| 4,814,536 A | 3/1989 | Yurchak | 5,188,725 A | 2/1993 | Harandi |
| 4,849,562 A | 7/1989 | Buhs et al. | 5,191,142 A | 3/1993 | Marshall et al. |
| 4,849,573 A | 7/1989 | Kaeding | 5,194,244 A | 3/1993 | Brownscombe et al. |
| 4,851,602 A | 7/1989 | Harandi et al. | 5,202,506 A | 4/1993 | Kirchner et al. |
| 4,851,606 A | 7/1989 | Ragonese et al. | 5,202,511 A | 4/1993 | Salinas, III et al. |
| 4,886,925 A | 12/1989 | Harandi | 5,208,402 A | 5/1993 | Wilson |
| 4,886,932 A | 12/1989 | Leyshon | 5,210,357 A | 5/1993 | Kolts et al. |
| 4,891,463 A | 1/1990 | Chu | 5,215,648 A | 6/1993 | Zones et al. |
| 4,895,995 A | 1/1990 | James, Jr. et al. | 5,223,471 A | 6/1993 | Washecheck |
| 4,899,000 A | 2/1990 | Stauffer | 5,228,888 A | 7/1993 | Gmelin et al. |
| 4,899,001 A | 2/1990 | Kalnes et al. | 5,233,113 A | 8/1993 | Periana et al. |
| 4,899,002 A | 2/1990 | Harandi et al. | 5,237,115 A | 8/1993 | Makovec et al. |
| 4,902,842 A | 2/1990 | Kalnes et al. | 5,243,098 A | 9/1993 | Miller et al. |
| 4,925,995 A | 5/1990 | Robschlager | 5,243,114 A | 9/1993 | Johnson et al. |
| 4,929,781 A | 5/1990 | James, Jr. et al. | 5,245,109 A | 9/1993 | Kaminsky et al. |
| 4,939,310 A | 7/1990 | Wade | 5,254,772 A | 10/1993 | Dukat et al. |
| 4,939,311 A | 7/1990 | Washecheck et al. | 5,254,790 A | 10/1993 | Thomas et al. |
| 4,939,314 A | 7/1990 | Harandi et al. | 5,264,635 A | 11/1993 | Le et al. |
| 4,945,175 A | 7/1990 | Hobbs et al. | 5,268,518 A | 12/1993 | West et al. |
| 4,950,811 A | 8/1990 | Doussain et al. | 5,276,226 A | 1/1994 | Horvath et al. |
| 4,950,822 A | 8/1990 | Dileo et al. | 5,276,240 A | 1/1994 | Timmons et al. |
| 4,956,521 A | 9/1990 | Volles | 5,276,242 A | 1/1994 | Wu |
| 4,962,252 A | 10/1990 | Wade | 5,284,990 A | 2/1994 | Peterson et al. |
| 4,973,776 A | 11/1990 | Allenger et al. | 5,300,126 A | 4/1994 | Brown et al. |
| 4,973,786 A | 11/1990 | Karra | 5,306,855 A | 4/1994 | Periana et al. |
| 4,982,024 A | 1/1991 | Lin et al. | 5,316,995 A | 5/1994 | Kaminsky et al. |
| 4,982,041 A | 1/1991 | Campbell | 5,319,132 A | 6/1994 | Ozawa et al. |
| 4,988,660 A | 1/1991 | Campbell | 5,334,777 A | 8/1994 | Miller et al. |
| 4,990,696 A | 2/1991 | Stauffer | 5,345,021 A | 9/1994 | Casci et al. |
| 4,990,711 A | 2/1991 | Chen et al. | 5,354,916 A | 10/1994 | Horvath et al. |
| 5,001,293 A | 3/1991 | Nubel et al. | 5,354,931 A | 10/1994 | Jan et al. |
| 5,004,847 A | 4/1991 | Beaver et al. | 5,366,949 A | 11/1994 | Schubert |
| 5,013,424 A | 5/1991 | James, Jr. et al. | 5,371,313 A | 12/1994 | Ostrowicki |
| 5,013,793 A | 5/1991 | Wang et al. | 5,382,704 A | 1/1995 | Krespan et al. |
| 5,019,652 A | 5/1991 | Taylor et al. | 5,382,743 A | 1/1995 | Beech, Jr. et al. |
| 5,026,934 A | 6/1991 | Bains et al. | 5,382,744 A | 1/1995 | Abbott et al. |
| 5,026,937 A | 6/1991 | Bricker | 5,385,650 A | 1/1995 | Howarth et al. |
| 5,026,944 A | 6/1991 | Allenger et al. | 5,385,718 A | 1/1995 | Casci et al. |
| 5,034,566 A | 7/1991 | Ishino et al. | 5,395,981 A | 3/1995 | Marker |
| 5,043,502 A | 8/1991 | Martindale et al. | 5,399,258 A | 3/1995 | Fletcher et al. |
| 5,055,235 A | 10/1991 | Brackenridge et al. | 5,401,890 A | 3/1995 | Parks |
| 5,055,625 A | 10/1991 | Neidiffer et al. | 5,401,894 A | 3/1995 | Brasier et al. |
| 5,055,633 A | 10/1991 | Volles | 5,406,017 A | 4/1995 | Withers, Jr. |
| 5,055,634 A | 10/1991 | Volles | 5,411,641 A | 5/1995 | Trainham, III et al. |
| 5,059,744 A | 10/1991 | Harandi et al. | 5,414,173 A | 5/1995 | Garces et al. |
| 5,068,478 A | 11/1991 | Miller et al. | 5,430,210 A | 7/1995 | Grasselli et al. |
| 5,071,449 A | 12/1991 | Sircar | 5,430,214 A | 7/1995 | Smith et al. |
| 5,071,815 A | 12/1991 | Wallace et al. | 5,430,219 A | 7/1995 | Sanfilippo et al. |
| 5,073,656 A | 12/1991 | Chafin et al. | 5,433,828 A | 7/1995 | van Velzen et al. |
| 5,073,657 A | 12/1991 | Warren | 5,436,378 A | 7/1995 | Masini et al. |
| 5,082,473 A | 1/1992 | Keefer | 5,444,168 A | 8/1995 | Brown |
| 5,082,816 A | 1/1992 | Teller et al. | 5,446,234 A | 8/1995 | Casci et al. |
| 5,085,674 A | 2/1992 | Leavitt | 5,453,557 A | 9/1995 | Harley et al. |
| 5,087,779 A | 2/1992 | Nubel et al. | 5,456,822 A | 10/1995 | Marcilly et al. |
| 5,087,786 A | 2/1992 | Nubel et al. | 5,457,255 A | 10/1995 | Kumata et al. |
| 5,087,787 A | 2/1992 | Kimble et al. | 5,464,799 A | 11/1995 | Casci et al. |
| 5,093,533 A | 3/1992 | Wilson | 5,465,699 A | 11/1995 | Voigt |
| 5,093,542 A | 3/1992 | Gaffney | 5,470,377 A | 11/1995 | Whitlock |
| 5,096,469 A | 3/1992 | Keefer | 5,480,629 A | 1/1996 | Thompson et al. |

| | | | | | | |
|---|---|---|---|---|---|---|
| 5,486,627 | A | 1/1996 | Quarderer, Jr. et al. | 6,087,294 | A | 7/2000 | Klabunde et al. |
| 5,489,719 | A | 2/1996 | Le et al. | 6,090,312 | A | 7/2000 | Ziaka et al. |
| 5,489,727 | A | 2/1996 | Randolph et al. | 6,093,306 | A | 7/2000 | Hanrahan et al. |
| 5,500,297 | A | 3/1996 | Thompson et al. | 6,096,932 | A | 8/2000 | Subramanian |
| 5,510,525 | A | 4/1996 | Sen et al. | 6,096,933 | A | 8/2000 | Cheung et al. |
| 5,523,503 | A | 6/1996 | Funk et al. | 6,103,215 | A | 8/2000 | Zones et al. |
| 5,525,230 | A | 6/1996 | Wrigley et al. | 6,107,561 | A | 8/2000 | Thompson |
| 5,538,540 | A | 7/1996 | Whitlock | 6,117,371 | A | 9/2000 | Mack |
| 5,563,313 | A | 10/1996 | Chung et al. | 6,124,514 | A | 9/2000 | Emmrich et al. |
| 5,565,092 | A | 10/1996 | Pannell et al. | 6,127,588 | A | 10/2000 | Kimble et al. |
| 5,565,616 | A | 10/1996 | Li et al. | 6,130,260 | A | 10/2000 | Hall et al. |
| 5,571,762 | A | 11/1996 | Clerici et al. | 6,143,939 | A | 11/2000 | Farcasiu et al. |
| 5,571,885 | A | 11/1996 | Chung et al. | 6,169,218 | B1 | 1/2001 | Hearn et al. |
| 5,599,381 | A | 2/1997 | Whitlock | 6,180,841 | B1 | 1/2001 | Fatutto et al. |
| 5,600,043 | A | 2/1997 | Johnston et al. | 6,187,871 | B1 | 2/2001 | Thompson et al. |
| 5,600,045 | A | 2/1997 | Van Der Aalst et al. | 6,187,983 | B1 | 2/2001 | Sun |
| 5,609,654 | A | 3/1997 | Le et al. | 6,203,712 | B1 | 3/2001 | Bronner et al. |
| 5,633,419 | A | 5/1997 | Spencer et al. | 6,207,864 | B1 | 3/2001 | Henningsen et al. |
| 5,639,930 | A | 6/1997 | Penick | 6,225,517 | B1 | 5/2001 | Nascimento et al. |
| 5,653,956 | A | 8/1997 | Zones | 6,248,218 | B1 | 6/2001 | Linkous et al. |
| 5,656,149 | A | 8/1997 | Zones et al. | 6,265,505 | B1 | 7/2001 | McConville et al. |
| 5,661,097 | A | 8/1997 | Spencer et al. | 6,281,405 | B1 | 8/2001 | Davis et al. |
| 5,663,465 | A | 9/1997 | Clegg et al. | 6,320,085 | B1 | 11/2001 | Arvai et al. |
| 5,663,474 | A | 9/1997 | Pham et al. | 6,337,063 | B1 | 1/2002 | Rouleau et al. |
| 5,675,046 | A | 10/1997 | Ohno et al. | 6,342,200 | B1 | 1/2002 | Rouleau et al. |
| 5,675,052 | A | 10/1997 | Menon et al. | 6,368,490 | B1 | 4/2002 | Gestermann |
| 5,679,134 | A | 10/1997 | Brugerolle et al. | 6,369,283 | B1 | 4/2002 | Guram et al. |
| 5,679,879 | A | 10/1997 | Mercier et al. | 6,372,949 | B1 | 4/2002 | Brown et al. |
| 5,684,213 | A | 11/1997 | Nemphos et al. | 6,376,731 | B1 | 4/2002 | Evans et al. |
| 5,693,191 | A | 12/1997 | Pividal et al. | 6,380,328 | B1 | 4/2002 | McConville et al. |
| 5,695,890 | A | 12/1997 | Thompson et al. | 6,380,423 | B2 | 4/2002 | Banning et al. |
| 5,698,747 | A | 12/1997 | Godwin et al. | 6,380,444 | B1 | 4/2002 | Bjerrum et al. |
| 5,705,712 | A | 1/1998 | Frey et al. | 6,395,945 | B1 | 5/2002 | Randolph |
| 5,705,728 | A | 1/1998 | Viswanathan et al. | 6,403,840 | B1 | 6/2002 | Zhou et al. |
| 5,705,729 | A | 1/1998 | Huang | 6,406,523 | B1 | 6/2002 | Connor et al. |
| 5,708,246 | A | 1/1998 | Camaioni et al. | 6,423,211 | B1 | 7/2002 | Randolph et al. |
| 5,720,858 | A | 2/1998 | Noceti et al. | 6,426,441 | B1 | 7/2002 | Randolph et al. |
| 5,728,897 | A | 3/1998 | Buysch et al. | 6,426,442 | B1 | 7/2002 | Ichikawa et al. |
| 5,728,905 | A | 3/1998 | Clegg et al. | 6,452,058 | B1 | 9/2002 | Schweizer et al. |
| 5,734,073 | A | 3/1998 | Chambers et al. | 6,455,650 | B1 | 9/2002 | Lipian et al. |
| 5,741,949 | A | 4/1998 | Mack | 6,462,243 | B1 | 10/2002 | Zhou et al. |
| 5,744,669 | A | 4/1998 | Kalnes et al. | 6,465,696 | B1 | 10/2002 | Zhou et al. |
| 5,750,801 | A | 5/1998 | Buysch et al. | 6,465,699 | B1 | 10/2002 | Grosso |
| 5,770,175 | A | 6/1998 | Zones | 6,472,345 | B2 | 10/2002 | Hintermann et al. |
| 5,776,871 | A | 7/1998 | Cothran et al. | 6,472,572 | B1 | 10/2002 | Zhou et al. |
| 5,780,703 | A | 7/1998 | Chang et al. | 6,475,463 | B1 | 11/2002 | Elomari et al. |
| 5,782,936 | A | 7/1998 | Riley | 6,475,464 | B1 | 11/2002 | Rouleau et al. |
| 5,798,314 | A | 8/1998 | Spencer et al. | 6,479,705 | B2 | 11/2002 | Murata et al. |
| 5,814,715 | A | 9/1998 | Chen et al. | 6,482,997 | B2 | 11/2002 | Petit-Clair et al. |
| 5,817,904 | A | 10/1998 | Vic et al. | 6,486,368 | B1 | 11/2002 | Zhou et al. |
| 5,821,394 | A | 10/1998 | Schoebrechts et al. | 6,491,809 | B1 | 12/2002 | Briot et al. |
| 5,847,224 | A | 12/1998 | Koga et al. | 6,495,484 | B1 | 12/2002 | Holtcamp |
| 5,849,978 | A | 12/1998 | Benazzi et al. | 6,509,485 | B2 | 1/2003 | Mul et al. |
| 5,866,735 | A | 2/1999 | Cheung et al. | 6,511,526 | B2 | 1/2003 | Jagger et al. |
| 5,882,614 | A | 3/1999 | Taylor, Jr. et al. | 6,514,319 | B2 | 2/2003 | Keefer et al. |
| 5,895,831 | A | 4/1999 | Brasier et al. | 6,518,474 | B1 | 2/2003 | Sanderson et al. |
| 5,898,086 | A | 4/1999 | Harris | 6,518,476 | B1 | 2/2003 | Culp et al. |
| 5,905,169 | A | 5/1999 | Jacobson | 6,525,228 | B2 | 2/2003 | Chauvin et al. |
| 5,906,892 | A | 5/1999 | Thompson et al. | 6,525,230 | B2 | 2/2003 | Grosso |
| 5,908,963 | A | 6/1999 | Voss et al. | 6,528,693 | B1 | 3/2003 | Gandy et al. |
| 5,928,488 | A | 7/1999 | Newman | 6,538,162 | B2 | 3/2003 | Chang et al. |
| 5,952,538 | A | 9/1999 | Vaughn et al. | 6,540,905 | B1 | 4/2003 | Elomari |
| 5,959,170 | A | 9/1999 | Withers, Jr. | 6,545,191 | B1 | 4/2003 | Stauffer |
| 5,968,236 | A | 10/1999 | Bassine | 6,547,958 | B1 | 4/2003 | Elomari |
| 5,969,195 | A | 10/1999 | Stabel et al. | 6,548,040 | B1 | 4/2003 | Rouleau et al. |
| 5,977,402 | A | 11/1999 | Sekiguchi et al. | 6,552,241 | B1 | 4/2003 | Randolph et al. |
| 5,983,476 | A | 11/1999 | Eshelman et al. | 6,566,572 | B2 | 5/2003 | Okamoto et al. |
| 5,986,158 | A | 11/1999 | Van Broekhoven et al. | 6,572,829 | B2 | 6/2003 | Linkous et al. |
| 5,994,604 | A | 11/1999 | Reagen et al. | 6,585,953 | B2 | 7/2003 | Roberts et al. |
| 5,998,679 | A | 12/1999 | Miller | 6,616,830 | B2 | 9/2003 | Elomari |
| 5,998,686 | A | 12/1999 | Clem et al. | 6,620,757 | B2 | 9/2003 | McConville et al. |
| 6,002,059 | A | 12/1999 | Hellring et al. | 6,632,971 | B2 | 10/2003 | Brown et al. |
| 6,015,867 | A | 1/2000 | Fushimi et al. | 6,635,793 | B2 | 10/2003 | Mul et al. |
| 6,018,088 | A | 1/2000 | Olah | 6,641,644 | B2 | 11/2003 | Jagger et al. |
| 6,022,929 | A | 2/2000 | Chen et al. | 6,646,102 | B2 | 11/2003 | Boriack et al. |
| 6,034,288 | A | 3/2000 | Scott et al. | 6,669,846 | B2 | 12/2003 | Perriello |
| 6,056,804 | A | 5/2000 | Keefer et al. | 6,672,572 | B2 | 1/2004 | Werlen |
| 6,068,679 | A | 5/2000 | Zheng | 6,679,986 | B1 | 1/2004 | Da Silva et al. |
| 6,072,091 | A | 6/2000 | Cosyns et al. | 6,680,415 | B1 | 1/2004 | Gulotty, Jr. et al. |

| | | |
|---|---|---|
| 6,692,626 B2 | 2/2004 | Keefer et al. |
| 6,692,723 B2 | 2/2004 | Rouleau et al. |
| 6,710,213 B2 | 3/2004 | Aoki et al. |
| 6,713,087 B2 | 3/2004 | Tracy et al. |
| 6,713,655 B2 | 3/2004 | Yilmaz et al. |
| RE38,493 E | 4/2004 | Keefer et al. |
| 6,723,808 B2 | 4/2004 | Holtcamp |
| 6,727,400 B2 | 4/2004 | Messier et al. |
| 6,740,146 B2 | 5/2004 | Simonds |
| 6,753,390 B2 | 6/2004 | Ehrman et al. |
| 6,765,120 B2 | 7/2004 | Weber et al. |
| 6,797,845 B1 | 9/2004 | Hickman et al. |
| 6,797,851 B2 | 9/2004 | Martens et al. |
| 6,821,924 B2 | 11/2004 | Gulotty, Jr. et al. |
| 6,822,123 B2 | 11/2004 | Stauffer |
| 6,822,125 B2 | 11/2004 | Lee et al. |
| 6,825,307 B2 | 11/2004 | Goodall |
| 6,825,383 B1 | 11/2004 | Dewkar et al. |
| 6,831,032 B2 | 12/2004 | Spaether |
| 6,838,576 B1 | 1/2005 | Wicki et al. |
| 6,841,063 B2 | 1/2005 | Elomari |
| 6,852,896 B2 | 2/2005 | Stauffer |
| 6,866,950 B2 | 3/2005 | Connor et al. |
| 6,869,903 B2 | 3/2005 | Matsunaga |
| 6,875,339 B2 | 4/2005 | Rangarajan et al. |
| 6,878,853 B2 | 4/2005 | Tanaka et al. |
| 6,888,013 B2 | 5/2005 | Paparatto et al. |
| 6,900,363 B2 | 5/2005 | Harth et al. |
| 6,902,602 B2 | 6/2005 | Keefer et al. |
| 6,903,171 B2 | 6/2005 | Rhodes et al. |
| 6,909,024 B1 | 6/2005 | Jones et al. |
| 6,921,597 B2 | 7/2005 | Keefer et al. |
| 6,933,417 B1 | 8/2005 | Henley et al. |
| 6,946,566 B2 | 9/2005 | Yaegashi et al. |
| 6,953,868 B2 | 10/2005 | Boaen et al. |
| 6,953,870 B2 | 10/2005 | Yan et al. |
| 6,953,873 B2 | 10/2005 | Cortright et al. |
| 6,956,140 B2 | 10/2005 | Ehrenfeld |
| 6,958,306 B2 | 10/2005 | Holtcamp |
| 6,984,763 B2 | 1/2006 | Schweizer et al. |
| 7,001,872 B2 | 2/2006 | Pyecroft et al. |
| 7,002,050 B2 | 2/2006 | Santiago Fernandez et al. |
| 7,011,811 B2 | 3/2006 | Elomari |
| 7,019,182 B2 | 3/2006 | Grosso |
| 7,026,145 B2 | 4/2006 | Mizrahi et al. |
| 7,026,519 B2 | 4/2006 | Santiago Fernandez et al. |
| 7,037,358 B2 | 5/2006 | Babicki et al. |
| 7,045,670 B2 | 5/2006 | Johnson et al. |
| 7,049,388 B2 | 5/2006 | Boriack et al. |
| 7,053,252 B2 | 5/2006 | Boussand et al. |
| 7,057,081 B2 | 6/2006 | Allison et al. |
| 7,060,865 B2 | 6/2006 | Ding et al. |
| 7,064,238 B2 | 6/2006 | Waycuilis |
| 7,064,240 B2 | 6/2006 | Ohno et al. |
| 7,067,448 B1 | 6/2006 | Weitkamp et al. |
| 7,083,714 B2 | 8/2006 | Elomari |
| 7,084,308 B1 | 8/2006 | Stauffer |
| 7,091,270 B2 | 8/2006 | Zilberman et al. |
| 7,091,387 B2 | 8/2006 | Fong et al. |
| 7,091,391 B2 | 8/2006 | Stauffer |
| 7,094,936 B1 | 8/2006 | Owens et al. |
| 7,098,371 B2 | 8/2006 | Mack et al. |
| 7,105,710 B2 | 9/2006 | Boons et al. |
| 7,138,534 B2 | 11/2006 | Forlin et al. |
| 7,141,708 B2 | 11/2006 | Marsella et al. |
| 7,145,045 B2 | 12/2006 | Harmsen et al. |
| 7,148,356 B2 | 12/2006 | Smith, III et al. |
| 7,148,390 B2 | 12/2006 | Zhou et al. |
| 7,151,199 B2 | 12/2006 | Martens et al. |
| 7,161,050 B2 | 1/2007 | Sherman et al. |
| 7,169,730 B2 | 1/2007 | Ma et al. |
| 7,176,340 B2 | 2/2007 | Van Broekhoven et al. |
| 7,176,342 B2 | 2/2007 | Bellussi et al. |
| 7,182,871 B2 | 2/2007 | Perriello |
| 7,193,093 B2 | 3/2007 | Murray et al. |
| 7,196,239 B2 | 3/2007 | Van Egmond et al. |
| 7,199,083 B2 | 4/2007 | Zevallos |
| 7,199,255 B2 | 4/2007 | Murray et al. |
| 7,208,641 B2 | 4/2007 | Nagasaki et al. |
| 7,214,750 B2 | 5/2007 | McDonald et al. |
| 7,220,391 B1 | 5/2007 | Huang et al. |
| 7,226,569 B2 | 6/2007 | Elomari |
| 7,226,576 B2 | 6/2007 | Elomari |
| 7,230,150 B2 | 6/2007 | Grosso et al. |
| 7,230,151 B2 | 6/2007 | Martens et al. |
| 7,232,872 B2 | 6/2007 | Shaffer et al. |
| 7,238,846 B2 | 7/2007 | Janssen et al. |
| 7,244,795 B2 | 7/2007 | Agapiou et al. |
| 7,244,867 B2 | 7/2007 | Waycuilis |
| 7,250,107 B2 | 7/2007 | Benazzi et al. |
| 7,250,542 B2 | 7/2007 | Smith, Jr. et al. |
| 7,252,920 B2 | 8/2007 | Kurokawa et al. |
| 7,253,327 B2 | 8/2007 | Janssens et al. |
| 7,253,328 B2 | 8/2007 | Stauffer |
| 7,265,193 B2 | 9/2007 | Weng et al. |
| 7,267,758 B2 | 9/2007 | Benazzi et al. |
| 7,268,263 B1 | 9/2007 | Frey et al. |
| 7,271,303 B1 | 9/2007 | Sechrist et al. |
| 7,273,957 B2 | 9/2007 | Bakshi et al. |
| 7,282,603 B2 | 10/2007 | Richards |
| 7,285,698 B2 | 10/2007 | Liu et al. |
| 7,304,193 B1 | 12/2007 | Frey et al. |
| 7,342,144 B2 | 3/2008 | Kaizik et al. |
| 7,348,295 B2 | 3/2008 | Zones et al. |
| 7,348,464 B2 | 3/2008 | Waycuilis |
| 7,357,904 B2 | 4/2008 | Zones et al. |
| 7,361,794 B2 | 4/2008 | Grosso |
| 7,365,102 B1 | 4/2008 | Weissman |
| 7,390,395 B2 | 6/2008 | Elomari |
| 7,560,607 B2 | 7/2009 | Waycuilis |
| 7,674,941 B2 | 3/2010 | Waycuilis et al. |
| 7,713,510 B2 | 5/2010 | Harrod et al. |
| 7,880,041 B2 | 2/2011 | Waycuilis |
| 8,008,535 B2 | 8/2011 | Waycuilis |
| 2002/0102672 A1 | 8/2002 | Mizrahi et al. |
| 2002/0193649 A1 | 12/2002 | O'Rear et al. |
| 2002/0198416 A1 | 12/2002 | Zhou et al. |
| 2003/0004380 A1 | 1/2003 | Grumann et al. |
| 2003/0065239 A1 | 4/2003 | Zhu |
| 2003/0069452 A1 | 4/2003 | Sherman et al. |
| 2003/0078456 A1 | 4/2003 | Yilmaz et al. |
| 2003/0120121 A1 | 6/2003 | Sherman et al. |
| 2003/0125589 A1 | 7/2003 | Grosso |
| 2003/0166973 A1 | 9/2003 | Zhou et al. |
| 2004/0006246 A1 | 1/2004 | Sherman et al. |
| 2004/0062705 A1 | 4/2004 | Leduc |
| 2004/0152929 A1 | 8/2004 | Clarke |
| 2004/0158107 A1 | 8/2004 | Aoki |
| 2004/0158108 A1 | 8/2004 | Snoble |
| 2004/0171779 A1 | 9/2004 | Matyjaszewski et al. |
| 2004/0187684 A1 | 9/2004 | Elomari |
| 2004/0188324 A1 | 9/2004 | Elomari |
| 2004/0220433 A1 | 11/2004 | Van Der Heide |
| 2005/0027084 A1 | 2/2005 | Clarke |
| 2005/0038310 A1 | 2/2005 | Lorkovic et al. |
| 2005/0042159 A1 | 2/2005 | Elomari |
| 2005/0047927 A1 | 3/2005 | Lee et al. |
| 2005/0148805 A1 | 7/2005 | Jones |
| 2005/0171393 A1 | 8/2005 | Lorkovic |
| 2005/0192468 A1 | 9/2005 | Sherman et al. |
| 2005/0215837 A1 | 9/2005 | Hoffpauir |
| 2005/0234276 A1 | 10/2005 | Waycuilis |
| 2005/0234277 A1 | 10/2005 | Waycuilis |
| 2005/0245771 A1 | 11/2005 | Fong et al. |
| 2005/0245772 A1 | 11/2005 | Fong |
| 2005/0245777 A1 | 11/2005 | Fong |
| 2005/0267224 A1 | 12/2005 | Herling |
| 2006/0025617 A1 | 2/2006 | Begley |
| 2006/0100469 A1 | 5/2006 | Waycuilis |
| 2006/0135823 A1 | 6/2006 | Jun |
| 2006/0138025 A1 | 6/2006 | Zones |
| 2006/0138026 A1 | 6/2006 | Chen |
| 2006/0149116 A1 | 7/2006 | Slaugh |
| 2006/0229228 A1 | 10/2006 | Komon |
| 2006/0229475 A1 | 10/2006 | Weiss et al. |
| 2006/0270863 A1 | 11/2006 | Reiling |
| 2006/0288690 A1 | 12/2006 | Elomari |
| 2007/0004955 A1 | 1/2007 | Kay |

| Publication No. | Date | Name | Country | Number | Date |
|---|---|---|---|---|---|
| 2007/0078285 A1 | 4/2007 | Dagle | GB | 883256 A | 11/1961 |
| 2007/0100189 A1 | 5/2007 | Stauffer | GB | 930341 A | 7/1963 |
| 2007/0129584 A1 | 6/2007 | Basset | GB | 950975 | 3/1964 |
| 2007/0142680 A1 | 6/2007 | Ayoub | GB | 950976 | 3/1964 |
| 2007/0148067 A1 | 6/2007 | Zones | GB | 991303 | 5/1965 |
| 2007/0148086 A1 | 6/2007 | Zones | GB | 995960 | 6/1965 |
| 2007/0149778 A1 | 6/2007 | Zones | GB | 1015033 | 12/1965 |
| 2007/0149789 A1 | 6/2007 | Zones | GB | 1104294 | 2/1968 |
| 2007/0149819 A1 | 6/2007 | Zones | GB | 1133752 | 11/1968 |
| 2007/0149824 A1 | 6/2007 | Zones | GB | 1172002 | 11/1969 |
| 2007/0149837 A1 | 6/2007 | Zones | GB | 1212240 | 11/1970 |
| 2007/0197801 A1 | 8/2007 | Bolk | GB | 1233299 | 5/1971 |
| 2007/0197847 A1 | 8/2007 | Liu | GB | 1253618 | 11/1971 |
| 2007/0213545 A1 | 9/2007 | Bolk | GB | 1263806 | 2/1972 |
| 2007/0238905 A1 | 10/2007 | Arredondo | GB | 1446803 | 8/1976 |
| 2007/0238909 A1 | 10/2007 | Gadewar et al. | GB | 1542112 | 3/1979 |
| 2007/0276168 A1 | 11/2007 | Garel | GB | 2095243 A | 9/1982 |
| 2007/0284284 A1 | 12/2007 | Zones | GB | 2095245 A | 9/1982 |
| 2008/0022717 A1 | 1/2008 | Yoshida et al. | GB | 2095249 A | 9/1982 |
| 2008/0152555 A1 | 6/2008 | Wang et al. | GB | 2116546 A | 9/1982 |
| 2008/0171898 A1 | 7/2008 | Waycuilis | GB | 2120249 A | 11/1983 |
| 2008/0183022 A1 | 7/2008 | Waycuilis | GB | 2185754 A | 7/1987 |
| 2008/0188697 A1 | 8/2008 | Lorkovic | GB | 2191214 A | 12/1987 |
| 2008/0200740 A1 | 8/2008 | Waycuilis | SU | 694483 A1 | 10/1979 |
| 2008/0275284 A1 | 11/2008 | Waycuilis | WO | 83/00859 | 3/1983 |
| 2009/0005620 A1 | 1/2009 | Waycuilis et al. | WO | 85/04863 | 11/1985 |
| 2009/0163749 A1 | 6/2009 | Li et al. | WO | 85/04867 | 11/1985 |
| 2009/0247796 A1 | 10/2009 | Waycuilis et al. | WO | 90/08120 | 7/1990 |
| 2009/0308759 A1 | 12/2009 | Waycuilis | WO | 90/08752 | 8/1990 |
| 2009/0312586 A1 | 12/2009 | Waycuilis et al. | WO | 91/18856 | 12/1991 |
| 2009/0326292 A1 | 12/2009 | Waycuilis | WO | 92/03401 | 3/1992 |
| 2010/0087686 A1 | 4/2010 | Fong et al. | WO | 92/12946 | 8/1992 |
| 2010/0096588 A1 | 4/2010 | Gadewar et al. | WO | 93/16798 | 9/1993 |
| 2010/0234637 A1 | 9/2010 | Fong et al. | WO | 96/22263 | 7/1996 |
| 2011/0015458 A1 | 1/2011 | Waycuilis et al. | WO | 97/44302 | 11/1997 |
| 2011/0071326 A1 | 3/2011 | Waycuilis | WO | 98/12165 | 3/1998 |
| 2011/0218374 A1 | 9/2011 | Waycuilis | WO | 99/07443 | 2/1999 |
| | | | WO | 00/07718 A1 | 2/2000 |
| FOREIGN PATENT DOCUMENTS | | | WO | 00/09261 A1 | 2/2000 |
| CA | 1101441 | 5/1981 | WO | 01/14300 A1 | 3/2001 |
| CA | 1202610 | 4/1986 | WO | 01/38275 A1 | 5/2001 |
| CA | 2542857 | 5/2005 | WO | 01/44149 A1 | 6/2001 |
| CA | 2236126 | 8/2006 | WO | 02/094749 A1 | 11/2002 |
| CA | 2203115 | 9/2006 | WO | 02/094750 A1 | 11/2002 |
| CA | 2510093 | 12/2006 | WO | 02/094751 A2 | 11/2002 |
| EP | 0164798 A1 | 12/1985 | WO | 02/094752 A1 | 11/2002 |
| EP | 0418971 A1 | 3/1991 | WO | 03/000635 A1 | 1/2003 |
| EP | 0418974 A1 | 3/1991 | WO | 03/002251 A2 | 1/2003 |
| EP | 0418975 A1 | 3/1991 | WO | 03/018524 A1 | 3/2003 |
| EP | 0510238 A1 | 10/1992 | WO | 03/020676 A1 | 3/2003 |
| EP | 0526908 A2 | 2/1993 | WO | 03/022827 A1 | 3/2003 |
| EP | 0346612 B1 | 8/1993 | WO | 03/043575 A2 | 5/2003 |
| EP | 0560546 A1 | 9/1993 | WO | 03/051813 A1 | 6/2003 |
| EP | 0976705 A1 | 2/2000 | WO | 03/062143 A1 | 7/2003 |
| EP | 1186591 A2 | 3/2002 | WO | 03/062172 A2 | 7/2003 |
| EP | 1253126 A1 | 10/2002 | WO | 03/078366 A1 | 9/2003 |
| EP | 1312411 A2 | 5/2003 | WO | 2004/018093 A2 | 3/2004 |
| EP | 1235769 B1 | 5/2004 | WO | 2004/067487 A2 | 8/2004 |
| EP | 1435349 A2 | 7/2004 | WO | 2005/014168 A1 | 2/2005 |
| EP | 1440939 A1 | 7/2004 | WO | 2005/019143 A1 | 3/2005 |
| EP | 1235772 B1 | 1/2005 | WO | 2005/021468 A1 | 3/2005 |
| EP | 1661620 A1 | 5/2006 | WO | 2005/035121 A2 | 4/2005 |
| EP | 1760057 A1 | 3/2007 | WO | 2005/037758 A1 | 4/2005 |
| EP | 1689728 B1 | 4/2007 | WO | 2005/054120 A2 | 6/2005 |
| EP | 1808227 A1 | 7/2007 | WO | 2005/056525 A2 | 6/2005 |
| EP | 1837320 A1 | 9/2007 | WO | 2005/058782 A1 | 6/2005 |
| GB | 5125 | 0/1912 | WO | 2005/090272 A1 | 9/2005 |
| GB | 156122 | 3/1922 | WO | 2005/095310 A2 | 10/2005 |
| GB | 294100 | 6/1929 | WO | 2005/104689 A2 | 11/2005 |
| GB | 363009 | 12/1931 | WO | 2005/105709 A1 | 11/2005 |
| GB | 402928 | 12/1933 | WO | 2005/105715 A1 | 11/2005 |
| GB | 474922 A | 11/1937 | WO | 2005/110953 A1 | 11/2005 |
| GB | 536491 | 5/1941 | WO | 2005/113437 A1 | 12/2005 |
| GB | 553950 | 6/1943 | WO | 2005/113440 A1 | 12/2005 |
| GB | 586483 | 3/1947 | WO | 2006/007093 A1 | 1/2006 |
| GB | 775590 | 5/1957 | WO | 2006/015824 A1 | 2/2006 |
| GB | 793214 | 4/1958 | WO | 2006/019399 A2 | 2/2006 |
| GB | 796048 | 6/1958 | WO | 2006/020234 A1 | 2/2006 |
| GB | 796085 | 6/1958 | WO | 2006/036293 A1 | 4/2006 |

| | | | |
|---|---|---|---|
| WO | 2006/039213 A1 | 4/2006 | |
| WO | 2006/039354 A2 | 4/2006 | |
| WO | 2006/043075 A1 | 4/2006 | |
| WO | 2006/053345 A1 | 5/2006 | |
| WO | 2006/067155 A2 | 6/2006 | |
| WO | 2006/067188 A1 | 6/2006 | |
| WO | 2006/067190 A1 | 6/2006 | |
| WO | 2006/067191 A1 | 6/2006 | |
| WO | 2006/067192 A1 | 6/2006 | |
| WO | 2006/067193 A1 | 6/2006 | |
| WO | 2006/069107 A2 | 6/2006 | |
| WO | 2006/071354 A1 | 7/2006 | |
| WO | 2006/083427 A2 | 8/2006 | |
| WO | 2006/100312 A2 | 9/2006 | |
| WO | 2006/104909 A2 | 10/2006 | |
| WO | 2006/104914 A1 | 10/2006 | |
| WO | 2006/111997 A1 | 10/2006 | |
| WO | 2006/113205 A2 | 10/2006 | |
| WO | 2006/118935 A2 | 11/2006 | |
| WO | 2007/001934 A2 | 1/2007 | |
| WO | 2007/017900 A2 | 2/2007 | |
| WO | 2007/044139 A1 | 4/2007 | |
| WO | 2007/046986 A2 | 4/2007 | |
| WO | 2007/050745 A1 | 5/2007 | |
| WO | 2007/071046 A1 | 6/2007 | |
| WO | 2007/079038 A2 | 7/2007 | |
| WO | 2007/091009 A2 | 8/2007 | |
| WO | 2007/094995 A2 | 8/2007 | |
| WO | 2007/107031 A1 | 9/2007 | |
| WO | 2007/111997 A2 | 10/2007 | |
| WO | 2007/114479 A1 | 10/2007 | |
| WO | 2007/125332 A1 | 11/2007 | |
| WO | 2007/130054 A1 | 11/2007 | |
| WO | 2007/130055 A1 | 11/2007 | |
| WO | 2007/141295 A1 | 12/2007 | |
| WO | 2007/142745 A1 | 12/2007 | |
| WO | 2008/036562 A1 | 3/2008 | |
| WO | 2008/036563 A2 | 3/2008 | |
| WO | 2008/106319 A1 | 9/2008 | |
| WO | 2008/157043 A1 | 12/2008 | |
| WO | 2008/157044 A1 | 12/2008 | |
| WO | 2008/157045 A1 | 12/2008 | |
| WO | 2008/157046 A1 | 12/2008 | |
| WO | 2008/157047 A1 | 12/2008 | |
| WO | 2009/152403 A1 | 12/2009 | |
| WO | 2009/152405 A1 | 12/2009 | |
| WO | 2009/152408 A1 | 12/2009 | |
| WO | 2010009376 A1 | 1/2010 | |
| WO | 2011/008573 A1 | 1/2011 | |
| WO | 2011109244 A2 | 9/2011 | |

OTHER PUBLICATIONS

U.S. Appl. No. 60/559,844, filed Apr. 6, 2004, Sherman et al.
U.S. Appl. No. 60/765,115, filed Feb. 3, 2006, Gadewar et al.
U.S. Office Communication from U.S. Appl. No. 10/365,346 dated Jun. 12, 2006.
U.S. Office Communication from U.S. Appl. No. 10/826,885 dated Oct. 31, 2005.
U.S. Office Communication from U.S. Appl. No. 10/826,885 dated Apr. 19, 2006.
U.S. Office Communication from U.S. Appl. No. 10/826,885 dated Jul. 27, 2006.
U.S. Office Communication from U.S. Appl. No. 10/826,885 dated Nov. 2, 2006.
U.S. Office Communication from U.S. Appl. No. 10/826,885 dated Jan. 24, 2007.
U.S. Office Communication from U.S. Appl. No. 10/893,418 dated Jun. 14, 2007.
U.S. Office Communication from U.S. Appl. No. 10/893,418 dated Jan. 2, 2008.
U.S. Office Communication from U.S. Appl. No. 11/091,130 dated Oct. 3, 2007.
U.S. Office Communication from U.S. Appl. No. 11/101,886 dated Jan. 24, 2007.
U.S. Office Communication from U.S. Appl. No. 11/254,438 dated Jan. 24, 2007.
U.S. Office Communication from U.S. Appl. No. 11/254,438 dated Nov. 1, 2007.
U.S. Office Communication from U.S. Appl. No. 11/778,479 dated Feb. 22, 2010.
U.S. Office Communication from U.S. Appl. No. 12/112,926 dated Jan. 16, 2009.
U.S. Office Communication from U.S. Appl. No. 12/112,926 dated Sep. 14, 2009.
U.S. Office Communication from U.S. Appl. No. 12/112,926 dated Jan. 7, 2010.
U.S. Office Communication from U.S. Appl. No. 12/112,926 dated Apr. 22, 2010.
U.S. Office Communication from U.S. Appl. No. 12/112,926 dated Jan. 7, 2011.
U.S. Office Communication from U.S. Appl. No. 12/123,924 dated Mar. 19, 2010.
U.S. Office Communication from U.S. Appl. No. 12/123,924 dated Aug. 30, 2010.
U.S. Office Communication from U.S. Appl. No. 12/139,135 dated Nov. 24, 2010.
U.S. Office Communication from U.S. Appl. No. 12/502,024 dated Oct. 26, 2010.
Adachi et al., Synthesis of sialyl lewis X ganglioside analogs containing a variable length spacer between the sugar and lipophilic moieties, J. Carbohydrate Chemistry, vol. 17, No. 4-5, 1998, pp. 595-607, XP009081720.
Akhrem et al., Ionic Bromination of Ethane and other alkanes (cycloalkanes) with bromine catalyzed by the polyhalomethane-2AlBr3 aprotic organic superacids under mild conditions, Tetrahedron Letters, vol. 36, No. 51, 1995, pp. 9365-9368, Pergamon, Great Britain.
Bagno et al., Superacid-catalyzed carbonylation of methane, methyl halides, methyl alcohol, and dimethyl ether to methyl acetate and acetic acid, J. Org. Chem. 1990, 55, pp. 4284-4289, Loker Hydrocarbon Research Institute; University of Southern California.
Bakker et al., An exploratory study of the addition reactions of ethyleheglycol, 2-chloroethanol and 1,3-dichloro-2-propanol to 1-dodecene, J. Am. Oil Chem. Soc., vol. 44, No. 9, 1967, pp. 517-521, XP009081570.
Benizri et al., Study of the liquid-vapor equilibrium in the bromine-hydrobrdmic acid-water system, Hydrogen Energy Vector, 1980, pp. 101-116.
Bouzide et al., Highly selective silver (I) oxide mediated monoprotection of symmetrical diols, Tetrahedron Letters, Elsevier, vol. 38, No. 34, 1997, pp. 5945-5948, XP004094157.
Bradshaw et al., Production of hydrobromic acid from bromine and methane for hydrogen production, Proceedings of the 2001 DOE Hydrogen Program Review, NREL/CP-570-30535, 2001, pp. 1-8.
Chang et al., The conversion of methanol and other O-compounds to hydrocarbons over zeolite catalysts, Journal of Catalysis 47, 1977, Academic Press, Inc., pp. 249-259.
Claude et al., Monomethyl-branching of long n-alkanes in the range from decane to tetracosane on Pt/H-ZSM-22 bifunctional catalyst, Journal of Catalysis 190, 2000, pp. 39-48.
Combined International Search Report and Written Opinion dated Apr. 17, 2007 for PCT/US2006/013394, Applicant: GRT, Inc., pp. 1-13.
Driscoll, Direct methane conversion, Federal Energy Technology Center, U.S. Department of Energy, M970779, pp. 1-10.
JLM Technology Ltd., The Miller GLS Technology for conversation of light hydrocarbons to alcohols, New Science for the Benefit of Humanity, May 31, 2000; pp. 1-10.
Kirk-Othmer, Encyclopedia of Chemical Technology, 4th Edition, vol. 1, A Wiley-Interscience Publication, John Wiley & Sons, 1991, pp. 946-997.
Liu et al., Higher hydrocarbons from methane condensation mediated by HBr, Journal of Molecular Catalysis A: Chemical 273, Elsevier B.V., 2007, pp. 14-20.
Loiseau et al., Multigram synthesis of well-defined extended bifunctional polyethylene glycol (PEG) chains, J. Org. Chem., vol. 69, No. 3, XO-002345040, 2004, pp. 639-647.

Lorkovic et al., A novel integrated process for the functionalization of methane and ethane: bromine as mediator, Catalysis Today 98, 2004, pp. 317-322.

Lorkovic et al., C1 oxidative coupling via bromine activation and tandem catalytic condensation and neutralization over CaO/zeolite composites II. Product distribution variation and full bromine confinement, Catalysis Today 98, 2004, pp. 589-594.

Lorkovic et al., C1 coupling via bromine activation and tandem catalytic condensation and neutralization over CaO/zeolite composites, Chem. Comm. 2004, pp. 566-567.

Mihai, et al., Application of Bronsted-type LFER in the study of the phospholipase C Mechanism, J. Am. Chem. Soc., vol. 125, No. 11, XP-002427777, 2003, pp. 3236-3242.

Mishakov et al., Nanocrystalline MgO as a dehydrohalogenation catalyst, Journal of Catalysis 206, Elsevier Science, USA, 2002, pp. 40-48.

Mochida, et al., The catalytic dehydrohalogenation of haloethanes on solid acids and bases, Bulletin of the Chemical Society of Japan, vol. 44, Dec. 1971, pp. 3305-3310.

Motupally et al., Recycling chlorine from hydrogen chloride, The Electrochemical Society Interface, Fall 1998, pp. 32-36.

Murray et al., Conversion of methyl halides to hydrocarbons on basic zeolites: a discovery by in situ NMR, J. Am. Chem. Soc., 1993, vol. 115, pp. 4732-4741.

Nishikawa et al., Ultrasonic relaxations in aqueous solutions of alcohols and the balance between hydrophobicity and hydrophilicity of the solutes, J. Phys. Chem., vol. 97, No. 14, XP-002427775, 1993, pp. 3539-3544.

Olah et al., Antimony pentafluoride/graphite catalyzed oxidative carbonylation of methyl halides with carbon monoxide and copper oxides (or copper/oxygen) to methyl acetate, J. Org. Chem. 1990, 55, pp. 4293-4297.

Olah et al., Antimony pentafluoride/graphite catalyzed oxidative conversion of methyl halides with copper oxides (or copper/oxygen) to dimethyl ether, J. Org. Chem. 1990, 55, pp. 4289-4293.

Olah, Electrophilic methane conversion, American Chemical Society, Acc. Chem. Res. 1987, 20, pp. 422-428.

Olah, Hydrocarbons through methane derivatives, Hydrocarbon Chemistry, 1995, pp. 89-90, John Wiley & Sons, Inc.

Olah et al., Hydrocarbons through methane derivatives, Hydrocarbon Chemistry, 2nd Edition, 2003, pp. 123, 149, and 153, John Wiley & Sons, Inc.

Olah et al., Onium Ylide Chemistry. 1. Bifunctional acid-base-catalyzed conversion of heterosubstituted methanes into ethylene and derived hydrocarbons. The Onium Ylide mechanism of the C1-C2 conversion. J. Am. Chem. Soc. 1984, 106, pp. 2143-2149.

Olah et al., Selective monohalogenation of methane over supported acid or platinum metal catalysts and hydrolysis of methyl halides over y-alumina-supported metal oxide/hydroxide catalysts. A feasible path for the oxidative conversion of methane into methyl alcohol/dimethyl ether., J. Am. Chem. Soc. 1985, 107, pp. 7097-7105.

Prelog et al., 234. Chirale 2, 2'-polyoxaalkano-9,9'-spirobifluorene, Helvetica Chimica ACTA, vol. 62, No. 7, 1979 pp. 2285-2302.

Rakoff et al., Quimica Organica Fundamental, Organic Chemistry, The Macmillan Company, 1966, pp. 58-63 and 76-77.

Richards, et al., Nanocrystalline ultra high surface area magnesium oxide as a selective base catalyst, Scripta Materialia, 44, 2001, pp. 1663-1666, Elsevier Science Ltd.

Shimizu et al., Gas-Phase electrolysis of hydrobromic acid using PTFE-bonded carbon electrode, Int. J. Hydrogen Energy, vol. 13, No. 6, pp. 345-349, 1988.

Smirnov et al., Selective bromination of alkanes and arylalkanes with CBr4, Mendeleev Commun., 2000, pp. 175-176.

Sun et al., Nanocrystal metal oxide—Chlorine adducts: selective catalysts for, chlorination of alkanes, J. Am. Chem. Soc., 1999, 121, pp. 5587-5588.

Sun et al., A general integrated process for synthesizing olefin oxides, Chem. Commun., The Royal Society of Chemistry 2004, pp. 2100-2101.

Tamura et al., The reactions of grignard reagents with transition metal halides: Coupling, disproportionation, and exchange with olefins, Bulletin of the Chemical Society of Japan, vol. 44, Nov. 1971, pp. 3063-3073.

Taylor et al., Direct conversion of methane to liquid hydrocarbons through chlorocarbon intermediates, 1988, Elsevier Science Publishers B.V. Amsterdam, Netherlands, pp. 483-489.

Taylor, Conversion of substituted methanes over ZSM-catalysts, 2000, pp. 3633-3638, Studies in Surface Science and Catalysis 130, Elsevier Science B.V.

Taylor, PETC's on-site naural gas conversion efforts, Preprints of the Fuel Division, 208th National Meeting of the American Chemical Society, 39 (4), 1994, pp. 1228-1232.

Thomas et al., Catalytically active centres in porous oxides: design and performance of highly selective new catalysts, Chem. Commun., 2001, pp. 675-687.

Thomas et al., Synthesis and characterization of a catalytically active nickel-silicoaluminophosphate catalyst for the conversion of methanol to ethene, American Chemical Society, 1991, 3, pp. 667-672.

Van Velzen et al., HBr electrolysis in the Ispra mark 13A flue gas desulphurization process: electrolysis in a DEM cell, Journal of Applied Electrochemistry, 20, 1990, pp. 60-68.

Wagner et al., Reactions of VX, GD, and HD with nanosize CaO: autocatalytic dehydrohalogenation of HD, J. Phys. Chem. B 2000, 104, pp. 5118-5123, 2000 American Chemical Society.

Wauters et al., Electrolytic membrane recovery of bromine from waste hydrogen bromide streams, AlChE Journal, Oct. 1998, vol. 44, No. 10, pp. 2144-2148.

Weissermel et al., Industrial Organic Chemistry, 3rd Edition, 1997, pp. 160-162, and 208.

Whitesides et al., Nuclear magnetic resonance spectroscopy. The effect of structure on magnetic nonequivalence due to molecular asymmetry, J. Am. Chem. Soc., vol. 86, No. 13, 1964, pp. 2628-2634, XP002427774.

Yilmaz et al., Bromine mediated partial oxidation of ethane over nanostructured zirconia supported metal oxide/bromide, Microporous and Mesoporous Materials, 79, 2005, Science Direct, Elsevier, pp. 205-214.

Zhou et al., An integrated process for partial oxidation of alkanes, Chem. Commun., 2003, The Royal Society of Chemistry, pp. 2294-2295.

ZSM-5 Catalyst, http://chemelba.ucsd.edu/methanol/memos/ZSM-5.html, Nov. 6, 2003, p. 1.

Abstract of GB 998681(A), Improvements in or relating to the recovery of bromine from bromine-containing materials, Publication date: Jul. 21, 1965, Applicant: Electro Chimie Metal+, espacenet worldwide database.

Abstract of JP 55-073619, Condensation of methyl chloride through dehydrochlorination, Publication date: Jun. 3, 1980, Inventor: Shigeo et al., http://www19.ipdl.inpit.go.jp/PA1/result....

U.S. Office Action from U.S. Appl. No. 12/139,135 dated Apr. 14, 2011.

Chretien; "Process for the Adjustment of the HHV in the LNG Plants"; 23rd World Gas Conference; Amsterdam 2006; Jun. 5-9, 2006; pp. 1-14.

U.S. Office Communication from U.S. Appl. No. 12/139,135 dated Oct. 14, 2011.

U.S. Office Communication from U.S. Appl. No. 12/477,307 dated Oct. 7, 2011.

Yang et al.; "Maximising the Value of Surplus Ethane and Cost-Effective Design to Handle Rich LNG"; publ. date Jun. 1, 2007; pp. 1-13.

Hannus; Adsorption and Transformation of Halogenated Hydrocarbons Over Zeolites, Applied Catalysis A: General 189, 1999, XP-002634422, pp. 263-276.

Howe; Zeolite Catalysts for Dehalogenation Processes, Applied Catalysis A: General 271, 2004, XP-002634421, pp. 3-11.

Li et al.; Pyrolysis of Halon 1301 Over Zeolite Catalysts, Microporous and Mesoporous Materials 35-36, 2000, XP-002634423, pp. 219-226.

U.S. Office Action Communication from U.S. Appl. No. 12/477,319 dated Jul. 22, 2011.

U.S. Office Action Communication from U.S. Appl. No. 12/502,024 dated May 31, 2011.

U.S. Office Action Communication from U.S. Appl. No. 12/502,024 dated Sep. 16, 2011.

Abstract of JP 8266888, Method for decomposing aromatic halogen compound, Publication date: Oct. 15, 1996, Inventor: Yuuji et al., esp@cenet database—worldwide.
Abstract of JP 2001031605, Production of 3-hydroxy-1-cycloalkene, Publication date: Feb. 6, 2001, Inventor: Hideo et al., esp@cenet database—worldwide.
Abstract of JP 2004-529189.
Abstract of JP 2004075683, Method for producing optically active halogenohydroxypropyl compound and glycidyl compound, Publication date: Mar. 11, 2004, Inventor: Keisuke et al., esp@cenet database—worldwide.
Abstract of JP 2004189655, Method for fluorinating with microwave, Publication date: Jul. 8, 2004, Inventor: Masaharu et al., esp@cenet database—worldwide.
Abstract of JP 2005075798, Method for producing adamantyl ester compound, Publication date: Mar. 24, 2005, Inventor: Norihiro et al., esp@cenet database—worldwide.
Abstract of JP 2005082563, Method for producing 1,3-adamantanediol, Publication date: Mar. 31, 2005, Inventor: Norihiro et al., esp@cenet database—worldwide.
Abstract of JP 2005145977, Process for catalytically oxidizing olefin and cycloolefin for the purpose of forming enol, olefin ketone, and epoxide, Publication date: Jun. 9, 2005, Inventor: Cancheng et al., esp@cenet database—worldwide.
Abstract of JP 2005254092, Method of manufacturing alkynes, Publication date: Sep. 22, 2005, Inventor: Shirakawa Eiji, esp@cenet database—worldwide.
Abstract of JP 2006151892, Preparation method of alcohol derivative, Publication date: Jun. 15, 2006, Inventor: Baba Akio et al., esp@cenet database—worldwide.
Abstract of JP 2006152263, Organic-inorganic hybrid-type mesoporous material, method for producing the same, and solid catalyst, Publication date: Jun. 15, 2006, Inventor: Junko et al., esp@cenet database—worldwide.
Abstract of JP 2006193473, Aryl polyadamantane derivative having carboxy or acid anhydride group and method for producing the same, Publication date: Jul. 27, 2006, Inventor: Yasuto et al, esp@cenet database—worldwide.
Abstract of JP 2006231318, Phosphorus containing macromolecule immobilizing palladium catalyst and method for using the same, Publication date: Sep. 7, 2006, Inventor: Osamu et al., esp@cenet database—worldwide.
Abstract of JP 2006263567, Optical resolution method of optical isomer and optical resolution device, Publication date: Oct. 5, 2006, Inventor: Yoshikazu et al., esp@cenet database—worldwide.
Abstract of JP 2006265157, Method for catalytically activating silicated nucleating agent using phosphazene base, Publication date: Oct. 5, 2006, Inventor: Yoshinori et al., esp@cenet database—worldwide.
Abstract of JP 2006306758, Method for producing biaryl compound, Publication date: Nov. 9, 2006, Inventor: Yuji et al., esp@cenet database—worldwide.
Abstract of JP 2007001942, Production method of para-xylene, Publication date: Jan. 11, 2007, Inventor: Kazuyoshi, esp@cenet database—worldwide.
Abstract of JP 2007015994, Method for synthesizing organic compound in ultra high rate under high temperature and high pressure water, and system of high temperature and high pressure reaction, Publication date: Jan. 25, 2007, Inventor: Hajime et al., esp@cenet database—worldwide.
Abstract of JP 2007045756, Hydrogenation method using diaphragm type hydrogenation catalyst, hydrogenation reaction apparatus and diaphragm type hydrogenation catalyst, Publication date: Feb. 22, 2007, Inventor: Shuji et al., esp@cenet database—worldwide.
Abstract of JP 2007061594, Method for decomposing organohalogen compound and mobile decomposition system, Publication date: Mar. 15, 2007, Inventor: Koichi et al., esp@denet database—worldwide.
Abstract of JP 2007099729, Method for producing alpha-methylstyrene or cumene, Publication date: Apr. 19, 2007, Inventor: Toshio, esp@cenet database—worldwide.
Abstract of RO 119778, Process for preparing perchloroethylene, Publication date: Mar. 30, 2005, Inventor: Horia et al., esp@cenet database—worldwide.

Abstract of WO 0105737, Method for preparing a carboxylic acid, Publication date: Jan. 25, 2001, Inventor: Pascal et al., esp@cenet database—worldwide.
Abstract of WO 0105738, Method for Preparing a carboxylic acid, Publication date: Jan. 25, 2001, Inventor: Pascal et al., esp@cenet database—worldwide.
Abstract of WO 9721656, Method for making fluoroalkanols, Publication date: Jun. 19, 1997, Inventor: Gillet, esp@cenet database—worldwide.
Abstract of WO 9950213, Method for producing dialkyl ethers, Publication date: Oct. 7, 1999, Inventor: Falkowski et al., esp@cenet database—worldwide.
Abstract of WO 2004092099, Method for producing cyclic enols, Publication date: Oct. 28, 2004, Inventor: Friedrich Marko et al., esp@cenet database—worldwide.
Abstract of WO 2006063852, Electroluminescent polymers and use thereof, Publication date: Jun. 22, 2006, Inventor: Buesing Arne et al., esp@cenet database—worldwide.
Abstract of WO 2006076942, Method for the production of synthetic fuels from oxygenates, Publication date: Jul. 27, 2006, Inventor: Rothaemel et al., esp@cenet database—worldwide.
Abstract of WO 2006136135, Method for decarboxylating C—C cross-linking of carboxylic acids with carbon electrophiles, Publication date: Dec. 28, 2006, Inventor: Goossen Lukas et al., esp@cenet database—worldwide.
Abstract of WO 2007028761, Method for chlorinating alcohols, Publication date: Mar. 15, 2007, Inventor: Rohde et al., esp@cenet database—worldwide.
Abstract of WO 2007128842, Catalytic transalkylation of dialkyl benzenes, Publication date: Nov. 15, 2007, Inventor: Goncalvesalmeida et al., esp@cenet database—worldwide.
Abstract of WO 2007137566, Method for catalytic conversion of organic oxygenated compounds from biomaterials, Publication date: Dec. 6, 2007, Inventor: Reschetilowski, esp@cenet database—worldwide.
Fenelonov, et al., Changes in texture and catalytic activity of nanocrystalline MgO during its transformation to MgCl2 in the reaction with 1-chlorobutane, J. Phys. Chem. B 2001., 105, 2001 American Chemical Society, pp. 3937-3941.
Final Report, Abstract, http://chemelab.ucsd.edu/methanol/memos/final.html, May 9, 2004, pp. 1-7.
Gibson, Phase-transfer synthesis of monoalkyl ethers of oligoethylene glycols, J. Org. Chem. 1980, vol. 45, No. 6, pp. 1095-1098, XP002427776.
http://webbook.nist.gov/, Welcome to the NIST chemistry webbook, Sep. 10, 2007, U.S. Secretary of Commerce on Behalf of the United States of America, pp. 1-2.
Ione, et al., Syntheses of hydrocarbons from compounds containing one carbon atom using bifunctional zeolite catalysts, Solid Fuel Chemistry, Khimiya Tverdogo Topliva, 1982, Allerton Press, Inc., vol. 16, No. 6, pp. 29-43.
Jaumain et al., Direct catalytic conversion of chloromethane to higher hydrocarbons over various protonic and cationic zeolite catalysts as studied by in-situ FTIR and catalytic testing, Studies in Surface Science and Catalysis 130, Elsevier Science B.V., 2000, pp. 1607-1612.
Abstract of BE 812868, Aromatic hydrocarbons prodn. from chlornated hydrocarbons, Publication date: Sep. 27, 1974, esp@cenet database—worldwide.
Abstract of BE 814900, Volatile aramatic cpds. prodn., Publication date: Sep. 2, 1974, esp@cenet database—worldwide.
Abstract of BR 0210054, Oxidative halogenation of C1 hydrocarbons to halogenated C1 hydrocarbons and integrated processes related thereto, Publication date: Aug. 17, 2004, Inventor: Schweizer et al., esp©cenet database—worldwide.
Abstract of CA 2447761 A1, Oxidative halogenation of C1 hydrocarbons to halogenated C1 hydrocarbons and integrated processes related thereto, Publication date: Nov. 28, 2002, Inventor: Hickman, et al.
Abstract of CA 2471295 A1, Integrated process for synthesizing alcohols, ethers, and olefins from alkanes, Publication date: Jul. 31, 2003, Inventor: Sherman et al.

Abstract of CN 1199039, Pentanol and its production process, Publication date: Nov. 18, 1998, Inventor: Kailun, esp@cenet database—worldwide.
Abstract of CN 1210847, Process for producing low carbon alcohol by directly hydrating low carbon olefines, Publication date: Mar. 17, 1999; Inventor: Zhenguo et al., esp@cenet database—worldwide.
Abstract of CN 1321728, Method for preparing aromatic hydrocarbon and hydrogen gas by using law-pressure gas, Publication date: Nov. 14, 2001, Inventor: Jie et al., esp@cenet database—worldwide.
Abstract of CN 1451721, Process for non-catalytic combustion deoxidizing coal mine gas for producing methanol, Publication date: Oct. 29, 2003, Inventor: Pengwan et al., esp@cenet database—worldwide.
Abstract of CN 1623969, Method for preparing 1, 4-benzene dime. thanol, Publication date: Jun. 8, 2005, Inventor. Jiarong et al., esp@cenet database—worldwide.
Abstract of CN 1657592, Method for converting oil to multiple energy fuel product, Publication date: Aug. 24, 2005, Inventor: Li, esp@cenet database—worldwide.
Abstract of CN 1687316, Method for producing biologic diesel oil from rosin, Publication date: Oct. 16, 2005, Inventor: Jianchun et al., esp@cenet database—worldwide.
Abstract of CN 1696248, Method for synthesizing biologic diesel oil based on ion liquid, Publication date: Nov. 16, 2005, Inventor: Sun, esp@cenet database—worldwide.
Abstract of CN 1699516, Process for preparing bio-diesel-oil by using miroalgae fat, Publication date: Nov. 23, 2005, Inventor: Miao, esp@cenet database—worldwide.
Abstract of CN 1704392, Process for producing alkylbenzene, Publcation date: Dec. 7, 2005, Inventor: Gao, esp@cenet database—worldwide.
Abstract of CN 1724612, Biological diesel oil catalyst and method of synthesizing biological diesel oil using sai catalyst, Publication date: Jan. 25, 2006; Inventor: Gu, esp©cenet database—worldwide.
Abstract of CN 1986737, Process for producing biodiesel oil with catering waste oil, Publication date: Jun. 27, 2007, Inventor. Chen, esp@cenet database—worldwide.
Abstract of CN 100999680, Esterification reaction tech. of preparing biodiesel by waste oil, Publication date: Jul. 18, 2007, Inventor: Weiming, esp@cenet database—worldwide.
Abstract of CN 101016229, Refining method for bromomeoamyl alcohol, Publication date: Aug. 15, 2007, Inventor: Tian, esp@cenet database—worldwide.
Abstract of DE 3209964, Process for the preparation of chlorinated hydrocarbons, Publication date: Nov. 11, 1982, Inventor: Pyke et al., esp@cenet database—worldwide.
Abstract of DE 3210196, Process for the preparation of a monochlorinated olefin, Publication date: Jan. 5, 1983, Inventor: Pyke et al., esp@cenet database—worldwide.
Abstract of DE 3226028, Process for the preparation of monochlorinated olefin, Publication date: Feb. 3, 1983, Inventor: Pyke et al., esp©cenet database—worldwide.
Abstract of DE 3334225, Process for the preparation of 1,2-dichloroethane, Publication date: Apr. 4, 1985, Inventor: Hebgen et al., esp@cenet database—worldwide.
Abstract of DE 4232056, 2,5-Di:methyl-hexane-2,5-di:ol continuous prodn. from tert. butanol—by oxidative dimerisation in two phase system with vigorous stirring; using aq. phase with specified density to facilitate phase sepn., Publication date: Mar. 31, 1994, Inventor: Gnann et al., esp@cenet database—worldwide.
Abstract of DE 4434823, Continuous prodn. of hydroxy-benzyl alkyl ether, Publication date: Apr. 4, 1996, Inventor: Stein et al., esp@cenet database—worldwide.
Abstract of EP 0021497 (A1), Synthesis of polyoxyalkylene glycol monoalkyl ethers., Publication date: Jan. 7, 1981, Inventor: Gibson, esp@cenet database—worldwide.
Abstract of EP 0039471, Process for the preparation of 2-chloro-1,1,1,2,3,3,3-heptafluoropropane., Publication date: Nov. 11, 1981, Inventor: Von Halasz, esp@cenet database—worldwide.
Abstract of EP 0101337, Process for the production of methylene chloride., Publication date: Feb. 22, 1984, Inventor: Olah et al., esp@cenet database—worldwide.

Abstract of EP 0235110, Process for the stabilization of silicalite catalysts., Publication date: Sep. 2, 1987, Inventor: Debras et al., esp@cenet databate—worldwide.
Abstract of EP 0407989, Method for the production of 1,1,1-trifluoro-2,2-dichloroethane by photochlorination., Publication date: Jan. 16, 1991, Inventor: Cremer el al., esp@cenet database—worldwide.
Abstract of EP 0442258, Process for the preparation of a polyunsaturated olefin., Publication date: Aug. 21, 1991, Inventor: Gaudin et al., esp@cenet database, worldwide.
Abstract of EP 0465294, Process for the preparation of unsaturated bromides., Publication date: Jan. 8, 1992, Inventor: Decaudin et al., esp@cenet database—worldwide.
Abstract of EP 0549387, Synthesis of n-perfluorooctylbromide., Publication date: Jun. 30, 1993, Inventor: Drivon et al., esp@cenet database—worldwide.
Abstract of EP 0850906, Process and apparatus for the etherification of olefinic hydrocarbon feedstocks, Publication date: Jul. 1, 1998, Inventor: Masson, esp@cenet database—worldwide.
Abstract of EP 0858987, Process for conversion of lighter alkanes to higher hydrocarbons, Publication date: Aug. 19, 1998, Inventor: Amariglio, et al., esp@cenet database—worldwide.
Abstract of EP 1395536, Oxidative halogenation of C1 hydrocarbons to halogenated C1 hydrocarbons and integrated processes related thereto, Publication date: Mar. 10, 2004, Inventor: Schweizer et al., esp@cenet database—worldwide.
Abstract of EP 1404636, Integrated process for synthesizing alcohols and ethers from alkanes, Publication date: Apr. 7, 2004, Inventor: Zhou et al., esp@cenet database—worldwide.
Abstract of EP 1435349 A2, Integrated process for synthesizing alcohols and ethers from alkanes, Publication date: Jul. 7, 2004, Inventor: Zhou et al.
Abstract of EP 1474371, Integrated process for synthesizing alcohols, ethers, and olefins from alkanes, Publication date: Nov. 10, 2004, Inventor: Zhou et al., esp@cenet database—worldwide.
Abstract of FR 2692259, Aromatisation of 2-4C hydrocarbons—using a fixed-mobile-catalytic bed process, Publication date: Dec. 17, 1993, Inventor: Alario et al., esp@cenet database—worldwide.
Abstract of FR 2880019, Manufacturing 1,2-dichloroethane, comprises cracking core hydrocarbonated source, separating into fractions, sending into chlorination reaction chamber and oxychlorination reaction chamber and separating from chambers, Publication date: Jun. 30, 2006, Inventor: Strebelle et al., esp@cenet database—worldwide.
Abstract of FR 2883870, Formation of 1,2-dichloroethane useful in manufacture of vinyl chloride involves subjecting mixture of cracking products obtained by cracking of hydrocarbon source, to a succession of aqueous quenching, alkaline washing, and oxidation steps, Publication date: Oct. 6, 2006, Inventor: Balthasart et al., esp@cenet database—worldwide.
Abstract of FR 2883871, Preparing 1,2-dichloroethane comprises cracking hydrocarbon to form mixture, sending mixture into storage reservoir, supplying mixture into chlorination and/or oxychloration reactor, and separating 1,2-dichloroethane from reactor, Publication date: Oct. 6, 2006, Inventor: Balthasart et al., esp@cenet database—worldwide.
Abstract of IT 1255246, Process for the preparation of dinitrodiphenylmethanes, Publication date: Oct. 20, 1995, Applicant: Enichem Spa et al., esp@cenet database—worldwide.
Abstract of IT 1255358, Process for the synthesis of 1,4-butanediol, Publication date: Oct. 31, 1995, Inventor: Ricci Marco, esp@cenet database—worldwide.
Abstract of JP 2142740, Production of fluoroalcohol, Publication date: May 31, 1990, Inventor: Tsutomu et al., esp@cenet database—worldwide.
Abstract of JP 2144150, Chemical process and catalyst used therefore, Publication date: Jun. 1, 1990, Inventor: Deidamusu et al., esp@cenet database—worldwide.
Abstract of JP 4305542, Production of halogenated hydrocarbon compounds, Publication date: Oct. 28, 1992, Inventor: Shinsuke et al., esp@cenet database—worldwide.

Abstract of JP 6172225, Method for fluorinating halogenated hydrocarbon, Publication date: Jun. 21, 1994, Inventor: Takashi et al., esp@cenet database—worldwide.

Abstract of JP 6206834, Production of Tetrachloroethanes, Publication date: Jul. 26, 1994, Inventor: Toshiro et al., esp@cenet database—worldwide.

US 8,198,495 B2

PROCESSES AND SYSTEMS FOR THE STAGED SYNTHESIS OF ALKYL BROMIDES

BACKGROUND OF THE INVENTION

The present invention relates to processes and systems for synthesizing alkyl bromides into high molecular weight hydrocarbons in at least two sequential or concurrent stages, and more particularly, in one or more embodiments, to processes and systems for synthesizing alkyl bromides in at least two sequential or concurrent stages operated with different feeds and at different temperatures.

Mono-halogenated alkanes may be used in the production of high molecular weight hydrocarbons, such as $C_{5+}$ gasoline-range and heavier hydrocarbons, as well as olefins, for example by conversion over an appropriate catalyst, such as a synthetic crystalline alumino-silicate catalyst, at sufficient temperatures to form high molecular-weight $C_{3+}$ hydrocarbons, the $C_{6+}$ fraction of which are predominately substituted aromatics. As the aromatic content of the $C_{6+}$ fraction of the high molecular weight hydrocarbons derived from such a process is higher than desired for production of "neat" gasoline motor fuel, the $C_{6+}$ fraction is valuable as a high-octane blending component with a petroleum-derived naphtha or natural gasoline derived from the processing of natural gas to produce a motor fuel. Petroleum-derived naphtha or natural gasoline derived from the processing of natural gas typically contain substantial paraffin content and have low octane ratings. Thus, a need exists for a process of synthesizing mono-halogenated alkanes over a suitable catalyst and at a suitable temperature to produce higher molecular-weight $C_{3+}$ hydrocarbons, the $C_{6+}$ fraction of which contains a substantial $C_{6+}$ paraffin content and thus a reduced aromatic content.

SUMMARY OF THE INVENTION

To achieve the foregoing and other objects, and in accordance with the purposes of the present invention, as embodied and broadly described herein, one characterization of the present invention is a process which comprises providing alkyl bromides and reacting at least a first portion of the alkyl bromides in the presence of a first catalyst and at a first temperature sufficient to form a first hydrocarbon product containing at least hydrocarbons having at least 5 carbon atoms and having a substantial $C_{6+}$ paraffin content. A second portion of the alkyl bromides is reacted in the presence of a second catalyst and at a second temperature sufficient to form a second hydrocarbon product containing at least hydrocarbons having at least 5 carbon atoms and having a substantial substituted aromatic content.

In another characterization of the present invention, a process comprises providing a first feed gas stream containing lower molecular weight alkanes and having from about 0.1 mol % to about 10.0 mol % $C_{2+}$ components and reacting bromine with the first feed gas stream to form first alkyl bromides. At least the first alkyl bromides may be reacted in the presence of a first catalyst and at a first temperature sufficient to form a first hydrocarbon product containing at least hydrocarbons having at least 5 carbon atoms and having a substantial $C_{6+}$ paraffin content. A second feed gas stream containing lower molecular weight alkanes and having predominately $C_{2+}$ components is reacted with bromine to form second alkyl bromides. At least the second alkyl bromides are reacted in the presence of a second catalyst and at a second temperature sufficient to form a second hydrocarbon product containing at least hydrocarbons having at least 5 carbon atoms and having a substantial substituted aromatic content.

In still another characterization of the present invention, a system is provided having a first synthesis zone and a second synthesis zone. The first synthesis zone contains a suitable catalyst and is configured to form at a first temperature hydrocarbon products containing paraffins from synthesis reactants comprising alkyl bromides. The second synthesis zone is in fluid communication with the first synthesis zone, contains a second suitable catalyst and is configured to form at a second temperature hydrocarbon products containing substituted aromatics from synthesis reactants comprising a unreacted portion of the alkyl bromides.

In a still further characterization of the present invention, a system is provided having a first bromination reactor, a first synthesis reactor, a second bromination reactor and a second synthesis reactor. The first bromination reactor is configured to form first bromination products comprising alkyl bromides from first bromination reactants comprising lower molecular weight alkanes having from about 0.1 mol % to about 10.0 mol % $C_{2+}$ components. The first synthesis reactor is in fluid communication with the first bromination reactor, contains a suitable catalyst and is configured to form hydrocarbon products containing paraffins from the first bromination products. The second bromination reactor is configured to form second bromination products comprising alkyl bromides from second bromination reactants comprising lower molecular weight alkanes containing predominately $C_{2+}$ components. The second synthesis reactor is in fluid communication with the second bromination reactor, contains a suitable catalyst and is configured to form hydrocarbon products containing substituted aromatics from the first bromination products. The second synthesis reactor is operated at a higher temperature than the first bromination reactor.

BRIEF DESCRIPTION OF THE DRAWINGS

The accompanying drawings, which are incorporated in and form a part of the specification, illustrate the embodiments of the present invention and, together with the description, serve to explain the principles of the invention.

In the drawings.

DETAILED DESCRIPTION OF THE PREFERRED EMBODIMENTS

Figure 1:
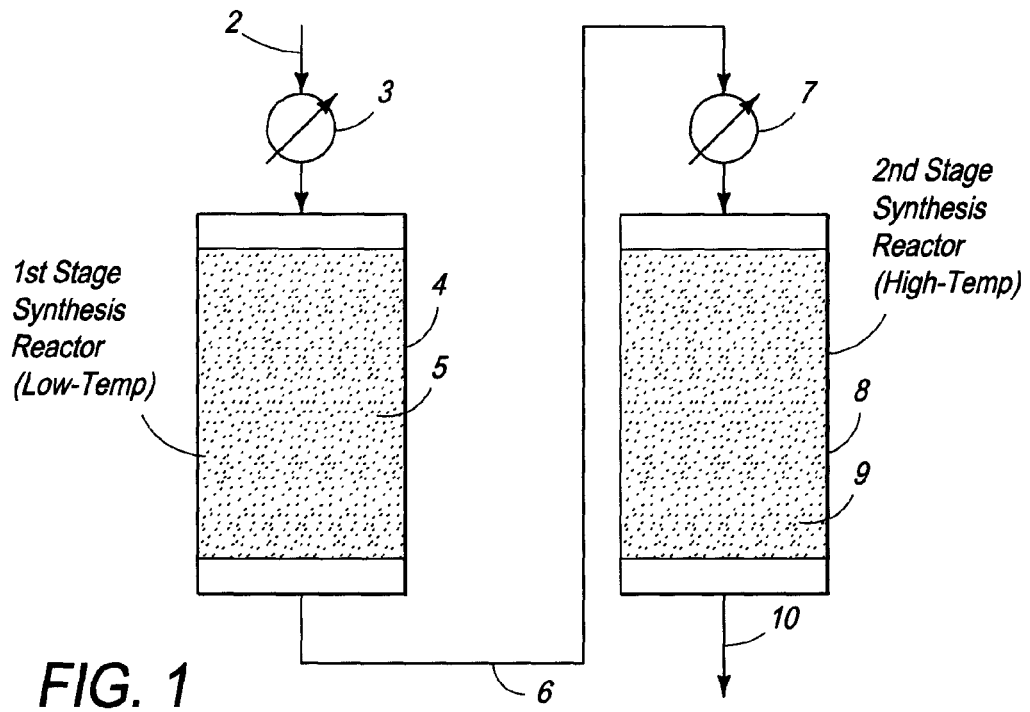
FIG. 1 is a simplified block flow diagram of one embodiment of the processes and systems of the present invention.

As used herein, the term "alkyl bromides" refers to mono-, di-, and tri-brominated lower molecular weight alkanes, and combinations of these. The term "high molecular weight hydrocarbons" as used herein refers to hydrocarbons comprising $C_3$ chains and longer hydrocarbon chains. In some embodiments, the high molecular weight hydrocarbons may be used directly as a product (e.g., LPG, motor fuel, etc.). In other instances, the high molecular weight hydrocarbons may be used as an intermediate product or as a feedstock for further processing. In other instances, the high molecular weight hydrocarbons may be further processed, for example, to produce gasoline grade fuels, diesel grade fuels, and fuel additives. In some embodiments, the high molecular weight hydrocarbons obtained by the processes of the present invention can be used directly as a motor gasoline fuel having a substantial paraffin content, as a fuel blending stock, or as feedstock for further processing, such as an aromatic feed to a process producing aromatic polymers such as polystyrene or related polymers, or an olefin feed to a process for producing polyolefins. The term "olefins" as used herein refers to hydrocarbons that contain two to six carbon atoms and at least one carbon-carbon double bond. The olefins may be further processed if desired. In some instances, the olefins produced by the processes of the present invention may be further reacted in a polymerization reaction (for example, a reaction using a metallocene catalyst) to produce poly(olefins), which may be useful in many end products such as plastics or synthetic lubricants.

The end use of the high molecular weight hydrocarbons, the olefins or mixtures thereof may depend on the particular catalyst employed in the synthesis portion of the processes and systems discussed below, as well as the operating parameters employed in the process. Other uses will be evident to those skilled in the art with the benefit of this disclosure.

Lower molecular weight alkanes may be used as a feed stock for the methods described herein. As utilized throughout this description, the term "lower molecular weight alkanes" refers to methane, ethane, propane, butane, pentane or mixtures of two or more of these individual alkanes. The lower molecular weight alkanes may be from any suitable source, for example, any source of gas that provides lower molecular weight alkanes, whether naturally occurring or synthetically produced. Examples of sources of lower molecular weight alkanes for use in the processes of the present invention include, but are not limited to, natural gas, coal-bed methane, regasified liquefied natural gas, gas derived from gas hydrates and/or chlathrates, gas derived from anerobic decomposition of organic matter or biomass, gas derived in the processing of tar sands, and synthetically produced natural gas or alkanes. Combinations of these may be suitable as well in some embodiments. In some embodiments, it may be desirable to treat the feed gas to remove undesirable compounds, such as sulfur compounds and carbon dioxide. In any event, it is important to note that small amounts of carbon dioxide, e.g., less than about 2 mol %, can be tolerated in the feed gas to the processes of the present invention.

Suitable sources of bromine that may be used in various embodiments of the present invention include, but are not limited to, elemental bromine, bromine salts, aqueous hydrobromic acid, metal bromide salts, and the like. Combinations may be suitable, but as recognized by those skilled in the art, using multiple sources may present additional complications. Certain embodiments of the methods and systems of the invention are described below. Although major aspects of what is to believed to be the primary chemical reactions involved in the methods are discussed in detail as it is believed that they occur, it should be understood that side reactions may take place. One should not assume that the failure to discuss any particular side reaction herein means that that reaction does not occur. Conversely, those that are discussed should not be considered exhaustive or limiting. Additionally, although figures are provided that schematically show certain aspects of the methods of the present invention, these figures should not be viewed as limiting on any particular method of the invention.

A block flow diagram generally depicting some aspects of certain embodiments of the processes and systems of the present invention is illustrated in FIG. 1. Alkyl bromides which are used as a feed in the embodiments depicted in FIG. 1 may be formed from brominating a feed gas stream containing lower molecular weight alkanes which is primarily methane with acceptable concentrations of $C_{2+}$ lower molecular weight alkane components. Such bromination may proceed thermally, catalytically or by a combination thereof. Typically, hydrogen bromide may also be formed in the bromination of lower molecular weight alkanes. In accordance with the embodiments of the processes of the present invention illustrated in FIG. 1, a gas stream 2 containing alkyl bromides may be cooled or heated by any suitable means, such as a heat exchanger 3, to about 150° C. to about 300° C., and more preferably from about 225° C. to about 275° C., before being introduced into to a first stage synthesis reactor 4. In the first stage synthesis reactor, the alkyl bromides are reacted exothermically at a temperature range of from about 150° C. to about 300° C., and more preferably from about 225° C. to about 275° C., and at a pressure in the range of about 1 to about 100 bar, over a suitable catalyst 5 to produce desired products (e.g., high molecular weight hydrocarbons, olefins or mixtures thereof). It is believed that at these conditions propyl bromide is more reactive than methyl bromide or ethyl bromide over a suitable catalyst thereby preferentially synthesizing the propyl units to form hydrocarbon products, for example high molecular weight hydrocarbons, olefins or mixtures thereof, that contain a substantial $C_{6+}$ paraffin content and thus a reduced aromatic content. In the first stage synthesis reactor 4, only a portion of the mono-brominated alkanes present in the alkyl bromides is converted, and any poly-brominated alkanes which may be present may have a lower propensity to be converted to heavy products or "coke" which deposit on the catalyst, due to the presence of propyl bromide and the lower temperature conditions.

The effluent 6 from the first stage synthesis reactor may be heated by any suitable means, such as a heat exchanger 7, before being introduced into a second stage synthesis reactor 8. In the second stage synthesis reactor, the methyl and ethyl bromides that are contained in the effluent are reacted exothermically at a temperature in the range of about 300° C. to about 450° C., and more preferably in the range of about 350° C. to about 425° C., and at a pressure in the range of about 1 to about 100 bar, over a suitable catalyst 9 to produce desired hydrocarbon products (e.g., high molecular weight hydrocarbons, olefins or mixtures thereof) which are removed as a hydrocarbon product stream 10 from second stage synthesis reactor 8. It is thought that at these conditions the methyl bromides and ethyl bromides may preferentially react over a suitable catalyst to oligomerize the methyl and ethyl units thereby forming products, for example high molecular weight hydrocarbons, olefins or mixtures thereof, that contain $C_{6+}$ fractions having primarily substituted aromatics and also light alkanes primarily in the $C_3$ to $C_{5+}$ range.

The catalyst used in the first and second stage synthesis reactors 4 and 8, respectively, may be any of a variety of suitable materials for catalyzing the conversion of the alkyl bromides to product hydrocarbons. In certain embodiments, the first and second stage synthesis reactors may comprise a fixed bed of the catalyst. A fluidized-bed of synthesis catalyst may also be used in certain circumstances, particularly in larger applications and may have certain advantages, such as constant removal of coke and a steady selectivity to product composition. Examples of suitable catalysts include a fairly wide range of materials that have the common functionality of being acidic ion-exchangers and which also contain a synthetic crystalline alumino-silicate oxide framework. In certain embodiments, a portion of the aluminum in the crystalline alumino-silicate oxide framework may be substituted with magnesium, boron, gallium and/or titanium. In certain embodiments, a portion of the silicon in the crystalline alumino-silicate oxide framework may be optionally substituted with phosphorus. The crystalline alumino-silicate catalyst generally may have a significant anionic charge within the crystalline alumino-silicate oxide framework structure which may be balanced, for example, by Na cations. Although zeolitic catalysts may be commonly obtained in a sodium form, a protonic or hydrogen form (via ion-exchange with ammonium hydroxide, and subsequent calcining) is preferred, or a mixed protonic/sodium form may also be used. The zeolite may also be modified by ion exchange with cations of other elements. Elements useful for ion exchange of the zeolite include $1^{st}$-row transition metals, Group 1 (IA), Group 2 (IIA), La, Ce, Mo, V, Ag or combinations thereof. Such subsequent ion-exchange, may replace the charge-balancing counter-ions, but furthermore may also partially replace ions in the oxide framework resulting in a modification of the crystalline make-up and structure of the oxide framework. The crystalline alumino-silicate or substituted crystalline alumino-silicate may include a microporous or mesoporous crystalline aluminosilicate, but, in certain embodiments, may include a synthetic microporous crystalline zeolite, and, for example, being of the MFI structure such as ZSM-5. Moreover, the crystalline alumino-silicate or substituted crystalline alumino-silicate, in certain embodiments, may be subsequently impregnated with an aqueous solution of a Mg, Ca, Sr, Ba, V, Ag, La or Ce salt, such as $Ce(NO_3)_3$, dried and calcined in air. In certain embodiments, the salts may be a halide salt, such as a bromide salt, such as MgBr2. Optionally, the crystalline alumino-silicate or substituted crystalline alumino-silicate may also contain between about 0.1 to about 1 weight % Pt, about 0.1 to 5 weight % Pd, or about 0.1 to about 5 weight % Ni in the metallic state. Although, such zeolite materials are primarily initially crystalline, it should be noted that some crystalline catalysts may undergo some loss of crystallinity either due to initial ion-exchange or impregnation or due to operation at the reaction conditions or during regeneration and hence my also contain significant amorphous character, yet still retain significant, and in some cases improved activity.

The particular catalyst 5 and 9 used in both the first and second stage synthesis reactors 4 and 8, respectively, will depend, for example, upon the particular product hydrocarbons that are desired. For example, when product hydrocarbons having primarily $C_3$, $C_4$ and $C_{5+}$ gasoline-range paraffinic compounds and heavier hydrocarbon fractions are desired, a ZSM-5 zeolite catalyst may be used. When it is desired to produce product hydrocarbons comprising a mixture of olefins and $C_{6+}$ products, an X-type or Y-type zeolite catalyst or SAPO zeolite catalyst may be used. Examples of suitable zeolites include an X-type, such as 10-X, or Y-type zeolite, although other zeolites with differing pore sizes and acidities, may be used in embodiments of the present invention. The catalyst used in the first and second stage synthesis reactors need not be identical so long as the catalyst used in both reactors are selected to form the similar products, e.g. selected to form hydrocarbons having primarily $C_3$, $C_4$ and $C_{5+}$ gasoline-range paraffinic compounds and heavier hydrocarbon fractions.

In addition to the catalyst, the temperature at which the first and second stage synthesis reactors are operated is an important parameter in determining the selectivity and conversion of the reaction to the particular product desired. For example, when a X type or Y type zeolite catalyst is used and it is desired to produce olefins, it may be advisable to operate the first stage synthesis reactor at a temperature within the range of about 250° C. to 400° C. and the second stage synthesis reactor at a temperature within the range of about 400° C. to 450° C. Alternatively, in an embodiment involving a ZSM-5 zeolite catalyst operating in a slightly lower temperature range of about 150° C. to 300° C. in the first stage synthesis reactor and about 300° C. to 400° C. in the second stage synthesis reactor, will result in the production of higher molecular weight hydrocarbons. In both instances, the high molecular weight hydrocarbon products produced by process and system of the present invention as illustrated in FIG. 1 will contain a substantial $C_{6+}$ paraffin content.

Figure 2:
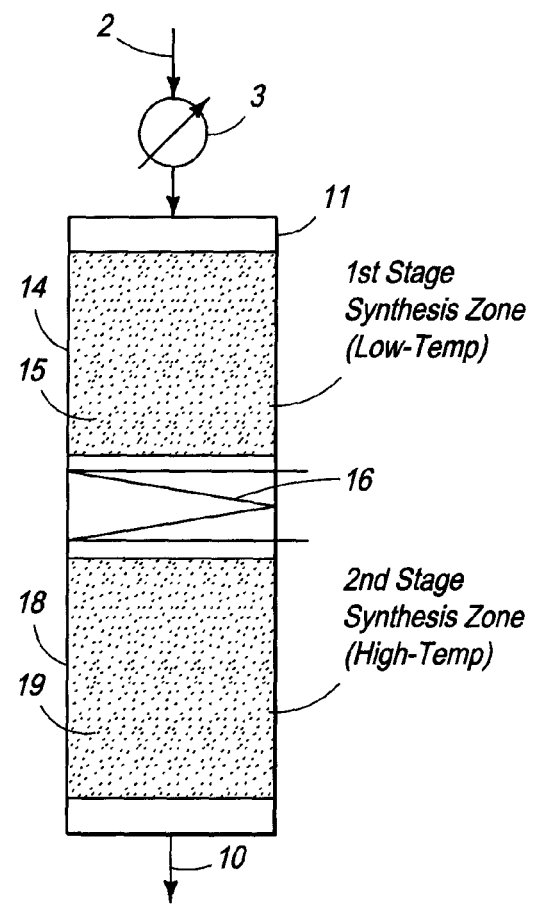
FIG. 2 is a schematic view of another embodiment of the processes and systems of the present invention.

A block flow diagram generally depicting some aspects of certain embodiments of the processes and systems of the present invention is illustrated in FIG. 2 and are similar to that illustrated in FIG. 1 and described above except that the first stage synthesis and the second stage synthesis are contained within distinct zones or beds 14 and 18, respectively, within the same reactor or vessel 11 containing suitable catalyst 15 and 19. Each zone or bed may be fixed or fluidized and the reactor may be provided with a suitable means for heating the effluent from the first stage synthesis zone or bed, such as an internal or external heat exchanger, prior to introducing the same to the second stage synthesis zone or bed within the same reactor. An internal exchanger 16 may be positioned between the first stage and the second stage synthesis zone or bed 14 and 18, respectively, as illustrated in FIG. 2. Where an external heater configuration is employed, an internal baffle may, for example, separate the two catalyst beds or zones contained within one reactor. Vapor effluent emanating from the first stage synthesis zone or bed located upstream of the internal baffle may be withdrawn via a suitable port or nozzle and heated in an external heat exchanger. The heated vapor may then be introduced to the reactor via a suitable port or nozzle below the internal baffle but above the second stage synthesis zone or bed. By combining the synthesis stages that are conducted in sequence into one reactor 11, equipment and operating costs are reduced.

Figure 3:
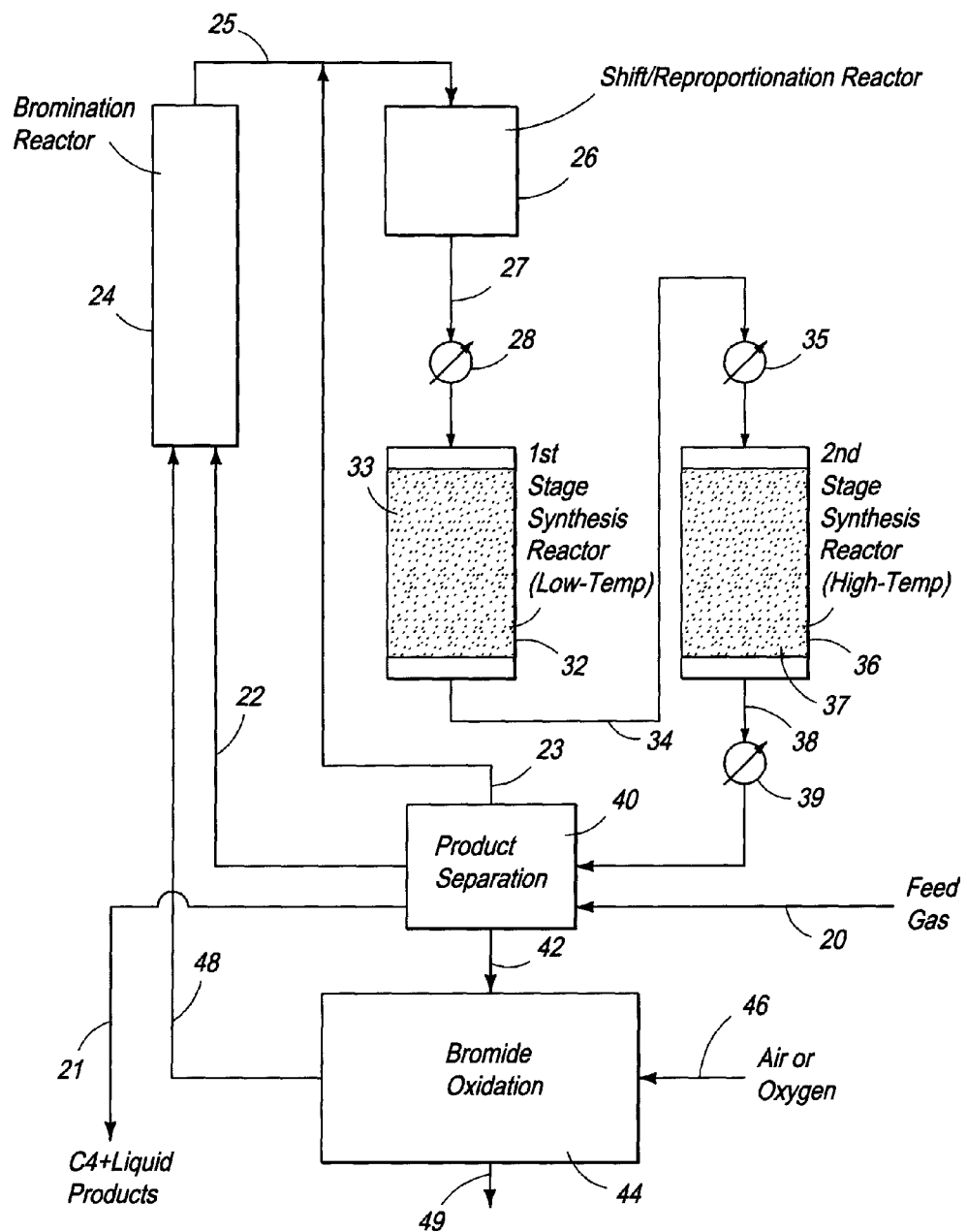
FIG. 3 is a schematic view of another embodiment of processes and systems of the present invention.

A block flow diagram generally depicting some aspects of certain embodiments of the processes and systems of the present invention is illustrated in FIG. 3. A feed gas stream 20 containing lower molecular weight alkanes may be pretreated to remove $C_{2+}$ components prior to being combined with bromine vapor and conveyed to a bromination reactor. The concentration of $C_{2+}$ components in the feed gas stream introduction into the bromination reactor may be from about 0.1 mol % to about 10.0 mol %, more preferably from about 0.1 mol % to about 1.0 mol %, and most preferably from about 0.1 mol % to about 0.5 mol %. While some $C_{2+}$ hydrocarbons may be tolerated in the bromination reactor in the embodiment of FIG. 3, higher concentrations thereof may result in the rapid formation of carbon-containing coke-like solids which may cause significant fouling and plugging in the bromination reactor as well as downstream components. As illustrated in FIG. 3, the feed gas stream may be combined with the effluent from the second stage synthesis reactor 36, product hydrocarbons and residual hydrocarbons, and pretreated in a product separation stage 40 to selectively remove $C_{2+}$ components and product hydrocarbons. More specifically, the feed gas, residual hydrocarbons and product hydrocarbons, e.g. high molecular weight hydrocarbons, olefins or mixtures thereof, may be conveyed to the product separation stage 40. The high molecular weight hydrocarbons, olefins or mixtures thereof as well as some $C_{2+}$ components may be then separated from the feed gas and process recycle gas to form a $C_{4+}$ liquid product stream 21. The feed gas and recycle gas are further processed to form a feed stream 22 for bromination reactor 24 and a gas stream 23 which is predominately C$_{3+}$ lower molecular weight alkane components with excess C$_2$ that is not able to be included in feed stream 22 due to C$_{2+}$ concentration limitations. The feed stream 22 which is primarily methane with acceptable concentrations of C$_{2+}$ lower molecular alkane components as noted above may be combined with bromine prior to, upon introduction into or within a bromination reactor. Gas stream 23 may be used in conjunction with a shift reactor 26 in a manner as hereinafter described, while the liquid hydrocarbon product 21 may be removed from the product separation stage for use or further petrochemical or fuel processing.

As illustrated in FIG. 3, the feed stream 22 containing predominantly methane and acceptable amounts of C$_{2+}$ lower molecular weight alkane components may be reacted exothermically in the bromination reactor with dry bromine vapor at a relatively low temperature in the range of about 250° C. to about 600° C., and at a pressure in the range of about 1 bar to about 30 bar to produce gaseous alkyl bromides and hydrogen bromide vapors. As will be evident to a skilled artisan with the benefit of this disclosure, the bromination reaction in bromination reactor 24 may be a homogeneous (thermal) reaction or a heterogeneous catalytic reaction. Non-limiting examples of suitable catalysts that may be used in first reactor 30 include platinum, palladium, or supported non-stiochiometric metal oxy-halides, such as FeO$_x$Br$_y$, or FeO$_x$Cl$_y$, or supported metal oxy-halides, such as TaOF$_3$, NbOF$_3$, ZrOF$_2$, SbOF$_3$ as described in Olah, et al., J. Am. Chem. Soc. 1985, 107, 7097-7105. The upper limit of the operating temperature range is greater than the upper limit of the reaction initiation temperature range to which the feed mixture is heated due to the exothermic nature of the bromination reaction. In the case of methane, the formation of methyl bromide is believed to occur in accordance with the following general reaction:

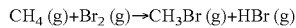

Due to the free-radical mechanism of the gas-phase bromination reaction, di-bromomethane and some tri-bromomethane and other poly-brominated lower molecular weight alkanes may be also formed. Bromination often occurs in the bromination reactor with a relatively high degree of selectivity to methyl bromide due to the alkane to bromine ratio employed. For example, in the case of the bromination of methane, a methane to bromine ratio of about 6:1 is believed to increase the selectivity to mono-halogenated methyl bromide to average approximately 88%, depending on reaction conditions, such as residence times less than about 15 seconds, temperature less than about 450° C., and extent of turbulent mixing. At these conditions, some dibromomethane and only extremely small amounts of tri-bromomethane approaching the detectable limits may also be formed in the bromination reaction. If a lower methane to bromine ratio of approximately 3 to 1 is utilized, selectivity to the mono-halogenated methyl bromide may fall to the range of approximately 65 to 75% at residence times less than about 15 seconds and temperatures less than about 450° C. However, methyl bromide selectivity may rise to approximately 90% if temperatures are increased to the range of about 490° C. to 530° C. and residence time is increased to about 60 seconds. However, at a methane to bromine ratio significantly less than about 2.5 to 1, unacceptably low selectivities to methyl bromide occurs, and, moreover, significant formation of undesirable di-bromomethane, tri-bromomethane, and carbon soot is observed. The relatively higher temperature range of about 450° C. to 530° C. employed in the bromination reactor also ensures that bromine is substantially consumed in the bromination reactor thereby effectively inhibiting subsequent formation of free-radical bromination in subsequent stages of the processes of the present invention due to the presence of elemental bromine. The residence time of the reactants in the bromination reactor necessary to achieve near-complete bromine reaction is relatively short and may be as little as 1-5 seconds under adiabatic reaction conditions. Any higher molecular weight alkanes, such as ethane, propane and butane that are contained in the feed gas to the bromination reactor may also be brominated, resulting in mono- and multiple-brominated species such as ethyl bromides, propyl bromides and butyl bromides. Further, in some embodiments, the dry bromine vapor that is fed into the bromination reactor may be substantially water-free. Applicant has discovered that, at least in some instances, this may be preferred because it appears that elimination of substantially all water vapor from the bromination step substantially eliminates the formation of unwanted carbon dioxide. This may increase the selectivity of alkane bromination to alkyl bromides, thus possibly eliminating the large amount of waste heat generated in the formation of carbon dioxide from alkanes.

Gas stream 23 may be combined with the effluent 25 withdrawn from the bromination reactor that comprises alkyl bromides, hydrogen bromide and unreacted bromine and introduced into a shift/reproportionation reactor 26. Further, although the bromine is generally rapidly reacted, any small amount of unreacted bromine which is not reacted in the bromination reactor due to imperfect mixing or shorter residence times and which may be present in the effluent from the bromination reactor is readily consumed by thermal bromination reaction with C$_{2+}$ hydrocarbons prior to or upon introduction into a shift/reproportionation reactor. In the shift/reproportionation reactor 26, a significant portion of the di- and tri-brominated alkanes that may be present in the alkyl bromides contained in the effluent 25 from the bromination reactor may be selectively converted upon reaction with C$_{2+}$ components to mono-brominated alkanes. As an example, where C$_3$ and di-bromomethane are the reactants, it is believed that the conversion occurs in accordance with the following general reaction:

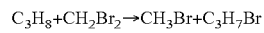

Although this reaction may proceed thermally without a catalyst, it has been determined that such thermal reaction requires unacceptably long residence time within the shift/reproportionation reactor and does not achieve satisfactory conversion rates to mono-brominated alkanes. Accordingly, it is preferred that the shift/reproportionation reactor contain a bed of suitable catalyst (not illustrated) selected from Group VIII metals, Group VIB metals, Group IB metals, aluminum, zinc, vanadium, magnesium, calcium, titanium, and mixtures thereof. Group VIII metals include iron, cobalt, nickel, platinum, palladium, rhodium, ruthenium, iridium, osmium or mixtures of two or more thereof. Group VIB metals include tungsten, molybdenum or chromium. Group IB metals include copper or silver. Preferably, the Group VIII metal used in this embodiment of the present invention is a noble metal selected from platinum, palladium, rhodium, ruthenium, iridium, osmium, or mixtures of two or more thereof, and more preferably the Group VIII metal is platinum. Most preferably, the Group VIII metal is iron employed as a metal bromide, metal oxide or non-stoichometric metal oxy-bromide. Preferably the Group VIB metals are molybdenum or tungsten. Preferably the Group IB metal is copper employed as a metal bromide, metal oxide or metal oxy-bromide. Non-limiting examples of suitable metal catalysts listed above which may form more than one thermally reversible bromide salt as used in the processes of the present invention are iron, molybdenum, tungsten, copper, vanadium, chromium or mixtures of two or more thereof. Nonlimiting examples of suitable catalysts listed above which may form single bromide salts as used in the processes of the present invention are cobalt, nickel, silver, zinc, magnesium, calcium, titanium, aluminum or mixtures of two or more thereof. These metals which form more than one thermally reversible bromide salt or a single bromide salt may be initially employed in the processes of the present invention as a bromide salt or an oxide since they would exist and function as bromides in the shift/reproportionation reactor due to conversion to bromide salts via a reaction with hydrogen bromide under the conditions employed in the shift/reproportionation reactor. Suitable supports are selected to have relatively low acidity to inhibit thermal decomposition and cracking of poly-brominated alkanes and have relatively low surface area to inhibit adsorption of the poly-brominated alkanes onto the support. Nonlimiting examples of suitable supports for use with the catalyst in the shift/reproportionation reactor are silica, titania, zirconia or low surface area alumina, preferably having a specific surface area less than about 50 m2/g.

The catalyst is loaded and dispersed upon a suitable support to yield high activity in a cost effective manner as will be evident to a skilled artisan. For example, it is preferred to use a loading of from about 0.1 wt % to about 1 wt % and more preferably from about 0.3 wt % to about 0.5 wt % when platinum is employed as the catalyst in the shift/reproportionation reactor bed, while a loading of from about 1 wt % to about 10 wt % and more preferably 3 wt % to about 10 wt % is employed when palladium is employed as the catalyst. In the case of the preferred non-noble metals such as iron, molybdenum, vanadium or mixtures thereof with higher loadings in the range of about 10% to about 20% or greater (as metal oxide) are cost-effective. When using a catalyst in the shift/reproportionation reactor 26, it is preferred to operate the reactor 26 at from about 200° C. to about 500° C., more preferably from about 300° C. to about 400° C. The residence time of the reactants in the shift/reproportionation reactor 26 necessary to achieve the desired selectivity to mono-brominated alkanes is relatively short and may be as little as 2 to 8 seconds.

The effluent 27 from shift/reproportionation reactor which contains alkyl bromides having a significantly increased ratio of mono-brominated alkanes to di- or tri-brominated alkanes may be cooled or heated by any suitable means, such as a heat exchanger 28, to about 150° C. to about 300° C., more preferably from about 225° C. to about 275° C., before being introduced into a first stage synthesis reactor 32. In the first stage synthesis reactor 32, the alkyl bromides may be reacted exothermically at a temperature range of from about 150° C. to about 300° C., and more preferably from about 225° C. to about 275° C., and at a pressure in the range of about 1 to about 100 bar, over a suitable catalyst 33 to produce desired hydrocarbons products (e.g., high molecular weight hydrocarbons, olefins or mixtures thereof). It is believed that at these conditions propyl bromide is more reactive than methyl bromide or ethyl bromide over a suitable catalyst thereby preferentially oligomerizing the propyl units thereby forming hydrocarbon products, for example high molecular weight hydrocarbons, olefins or mixtures thereof, that contain a substantial $C_{6+}$ paraffin content and thus a reduced aromatic content. In the first stage synthesis reactor 32, only a portion of the mono-brominated alkanes present in the alkyl bromides may be converted, and any poly-brominated alkanes which may be present may have a lower propensity to be converted to heavy products or "coke" which deposit on the catalyst, due to the presence of propyl bromide and the lower temperature conditions.

The effluent 34 from the first stage synthesis reactor may be heated by any suitable means, such as a heat exchanger 35, before being introduced into a second stage synthesis reactor 36. Effluent 34 contains hydrocarbon products and unreacted alkyl methyl and ethyl bromides. In the second stage synthesis reactor 36, the methyl and ethyl bromides may be reacted exothermically at a temperature in the range of about 300° C. to about 450° C., and more preferably in the range of about 350° C. to about 425° C., and at a pressure in the range of about 1 to about 100 bar, over a suitable catalyst to produce desired hydrocarbon products (e.g., high molecular weight hydrocarbons, olefins or mixtures thereof). It is believed that at these conditions the methyl bromides and ethyl bromides are reactive over a suitable catalyst to preferentially oligomerize the methyl and ethyl units thereby forming hydrocarbon products, for example high molecular weight hydrocarbons, olefins or mixtures thereof, that contain $C_{7+}$ fractions having primarily substituted aromatics and also light alkanes primarily in the $C_3$ to $C_{5+}$ range.

The catalyst 33 and 37 employed in the first and second stage synthesis reactors 32 and 36, respectively, may be any of a variety of suitable materials for catalyzing the conversion of the alkyl bromides to product hydrocarbons as previously set forth. In certain embodiments, the first and second stage synthesis reactors may comprise a fixed bed of the catalyst. A fluidized-bed of synthesis catalyst may also be used in certain circumstances, particularly in larger applications and may have certain advantages, such as constant removal of coke and a steady selectivity to product composition. The particular catalyst used in both the first and second stage synthesis reactors 32 and 36 will depend, for example, upon the particular product hydrocarbons that are desired. For example, when product hydrocarbons having primarily $C_3$, $C_4$ and $C_{5+}$ gasoline-range paraffinic compounds and heavier hydrocarbon fractions are desired, a ZSM-5 zeolite catalyst may be used. When it is desired to produce product hydrocarbons comprising a mixture of olefins and $C_{5+}$ products, an X-type or Y-type zeolite catalyst or SAPO zeolite catalyst may be used. Examples of suitable zeolites include an X-type, such as 10-X, or Y-type zeolite, although other zeolites with differing pore sizes and acidities, may be used in embodiments of the present invention. The catalyst used in the first and second stage synthesis reactors 32 and 36 need not be identical so long as the catalyst used in both reactors are selected to form the similar products, e.g. selected to form hydrocarbons having primarily $C_3$, $C_4$ and $C_{5+}$ gasoline-range paraffinic compounds and heavier hydrocarbon fractions.

The effluent 38 from the second stage synthesis reactor 36 may be cooled by suitable means such as heat exchanger 39 to recover heat for use elsewhere in the process, such as to produce steam or preheat feed to the process (not shown) or for other uses as determined by the skilled artisan, and then conveyed to a product separation stage 40. Hydrogen bromide may be removed from the hydrocarbon product, e.g. high molecular weight hydrocarbons, olefins or mixtures thereof, in the product separation stage and a stream 42 of separated hydrogen bromide may be conveyed to a bromide oxidation stage 44 wherein hydrogen bromide may be neutralized by a partially oxidized metal bromide salt to yield a metal bromide salt and steam. A stream 46 of oxygen or air may be introduced to the bromide oxidation stage 44 of the present invention to contact the resultant metal bromide salt so as to yield elemental bromine. A stream 48 of bromine may be recycled to the bromination stage as a dry bromine vapor and a partially oxidized metal bromide salt which may be used to neutralize and remove additional hydrogen bromide from the hydrocarbons produced by the process. The steam resulting from oxidation of the HBr with the partially oxidized metal bromide salt may be condensed, stripped of any residual bromine and withdrawn as a byproduct liquid water stream 49.

The first stage synthesis reactor 32 and the second stage synthesis reactor 36 of the process embodiments illustrated in FIG. 3 may be contained within distinct zones or beds within the same reactor as depicted in FIG. 2 and described above. Each zone or bed may be fixed or fluidized and the reactor may be provided with a suitable means for heating the effluent from the first stage synthesis zone or bed, such as an internal or external heat exchanger, prior to flowing the same to the second stage synthesis zone or bed within the same reactor.

Figure 4:
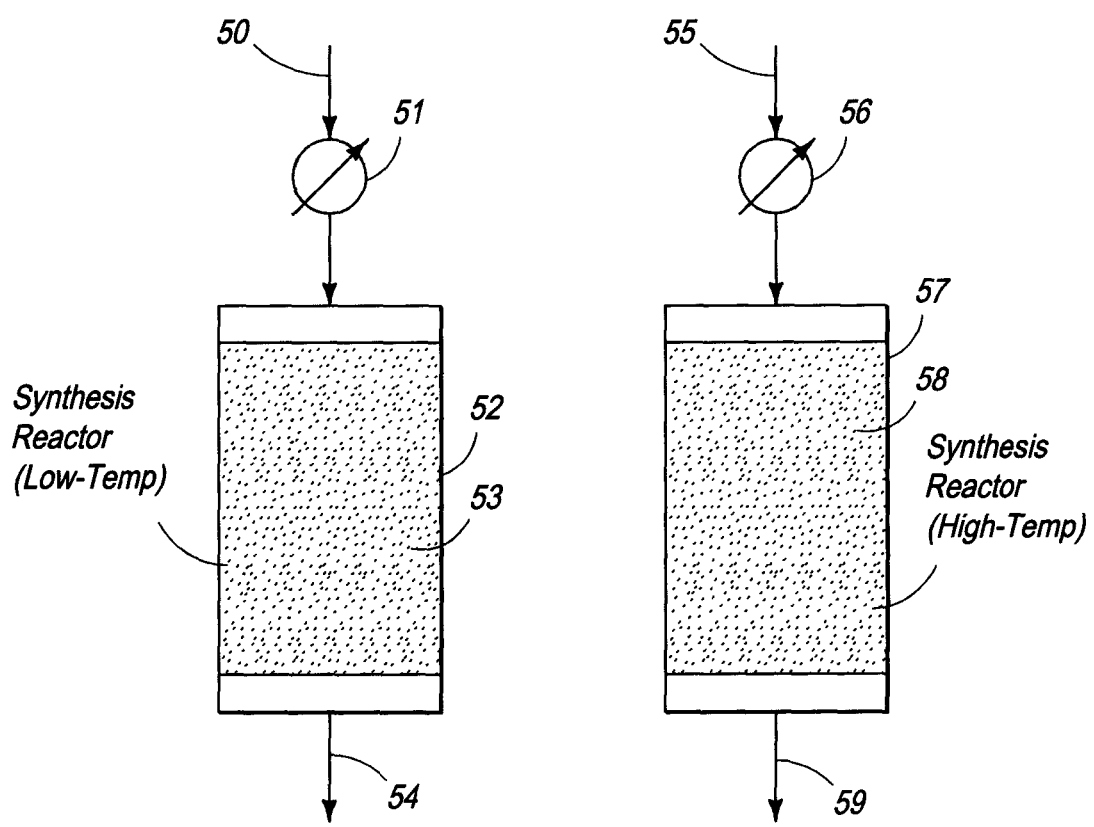
FIG. 4 is a schematic view of another embodiment of the processes and systems of the present invention.

A block flow diagram generally depicting some aspects of certain embodiments of the processes and systems of the present invention is illustrated in FIG. 4. While each of the embodiments illustrated in FIGS. 1-3 and discussed above employed first stage synthesis and the second stage synthesis reactors, zones or beds arranged in a series configuration, the embodiments of the processes and systems of the present invention illustrated generally in FIG. 4 depict a first synthesis reactor (low temperature) and a second synthesis (high temperature) reactor arranged in parallel. In such a parallel configuration, a stream 55 of alkyl bromides which are used as a feed to the second synthesis reactor in the embodiments depicted in FIG. 4 may be formed from brominating a feed gas stream containing lower molecular weight alkanes which is primarily methane with acceptable concentrations of $C_{2+}$ lower molecular alkane components. As discussed above with respect to FIGS. 1-3, the feed gas stream containing lower molecular weight alkanes may be pretreated to remove $C_{2+}$ components prior to being combined with bromine vapor and conveyed to a bromination reactor. The concentration of $C_{2+}$ components in the feed gas stream introduction into the bromination reactor may be from about 0.1 mol % to about 10.0 mol %, more preferably from about 0.1 mol % to about 1.0 mol %, and most preferably from about 0.1 mol % to about 0.5 mol %. While some $C_{2+}$ hydrocarbons may be tolerated in the bromination reactor in the embodiment of FIG. 3, higher concentrations thereof may result in the rapid formation of carbon-containing coke-like solids which cause fouling and plugging in the bromination reactor as well as downstream components. The steam 55 of $C_{1+}$ alkyl bromides are heated by any suitable means, such as a heat exchanger 56, before being introduced into a second synthesis reactor 57. In the second synthesis reactor 57, the methyl and ethyl bromides are reacted exothermically at a temperature in the range of about 300° C. to about 450° C., more preferably in the range of about 350° C. to about 425° C., and at a pressure in the range of about 1 to about 100 bar, over a suitable catalyst 58 to produce desired hydrocarbon products (e.g., high molecular weight hydrocarbons, olefins or mixtures thereof). It is believed that at these conditions the methyl bromides and ethyl bromides are reactive over a suitable catalyst 58 to oligomerize the methyl and ethyl units thereby forming a stream 59 of hydrocarbon products, for example high molecular weight hydrocarbons, olefins or mixtures thereof, that contain $C_{6+}$ fractions having primarily substituted aromatics and also light alkanes primarily in the $C_3$ to $C_{5+}$ range.

A separate stream 50 of predominately $C_{3+}$ alkyl bromides which are used as a feed to the first synthesis reactor 52 in the embodiments depicted in FIG. 4 may be formed from brominating a feed gas stream containing predominately $C_{3+}$ components, with acceptable amounts of $C_2$ components. The gas stream containing predominately $C_{3+}$ alkyl bromides may be cooled or heated by any suitable means, such as a heat exchanger, to about 150° C. to about 300° C., and more preferably from about 225° C. to about 275° C., before being introduced into to a first synthesis reactor 52. In the first synthesis reactor 52, the alkyl bromides are reacted exothermically at a temperature range of from about 150° C. to about 300° C., and more preferably from about 225° C. to about 275° C., and at a pressure in the range of about 1 to about 100 bar, over a suitable catalyst 53 to produce desired hydrocarbons products 54 (e.g., high molecular weight hydrocarbons, olefins or mixtures thereof). It is believed that at these conditions propyl bromide is more reactive than methyl bromide or ethyl bromide over a suitable catalyst thereby preferentially oligomerizing the propyl units thereby forming hydrocarbon products, for example high molecular weight hydrocarbons, olefins or mixtures thereof, that contain a substantial $C_{6+}$ paraffin content and thus a reduced aromatic content. In the first synthesis reactor 52, only a portion of the mono-brominated alkanes present in the alkyl bromides is converted, and any poly-brominated alkanes which may be present may have a lower propensity to be converted to heavy products or "coke" which deposit on the catalyst, due to the presence of propyl bromide and the lower temperature conditions.

As previously mentioned, the particular catalyst used in both the first and second synthesis reactors 52 and 57 of FIG. 4 will depend, for example, upon the particular product hydrocarbons that are desired. For example, when product hydrocarbons having primarily $C_3$, $C_4$ and $C_{5+}$ gasoline-range paraffinic compounds and heavier hydrocarbon fractions are desired, a ZSM-5 zeolite catalyst may be used. When it is desired to produce product hydrocarbons comprising a mixture of olefins and $C_{5+}$ products, an X-type or Y-type zeolite catalyst or SAPO zeolite catalyst may be used. Examples of suitable zeolites include an X-type, such as 10-X, or Y-type zeolite, although other zeolites with differing pore sizes and acidities, may be used in embodiments of the present invention. The catalyst used in the first and second stage synthesis reactors need not be identical, particularly in instances where the effluent from the first and second reactors contained different product hydrocarbons, are being further processed in a different manner, or both of the foregoing.

Figure 5:
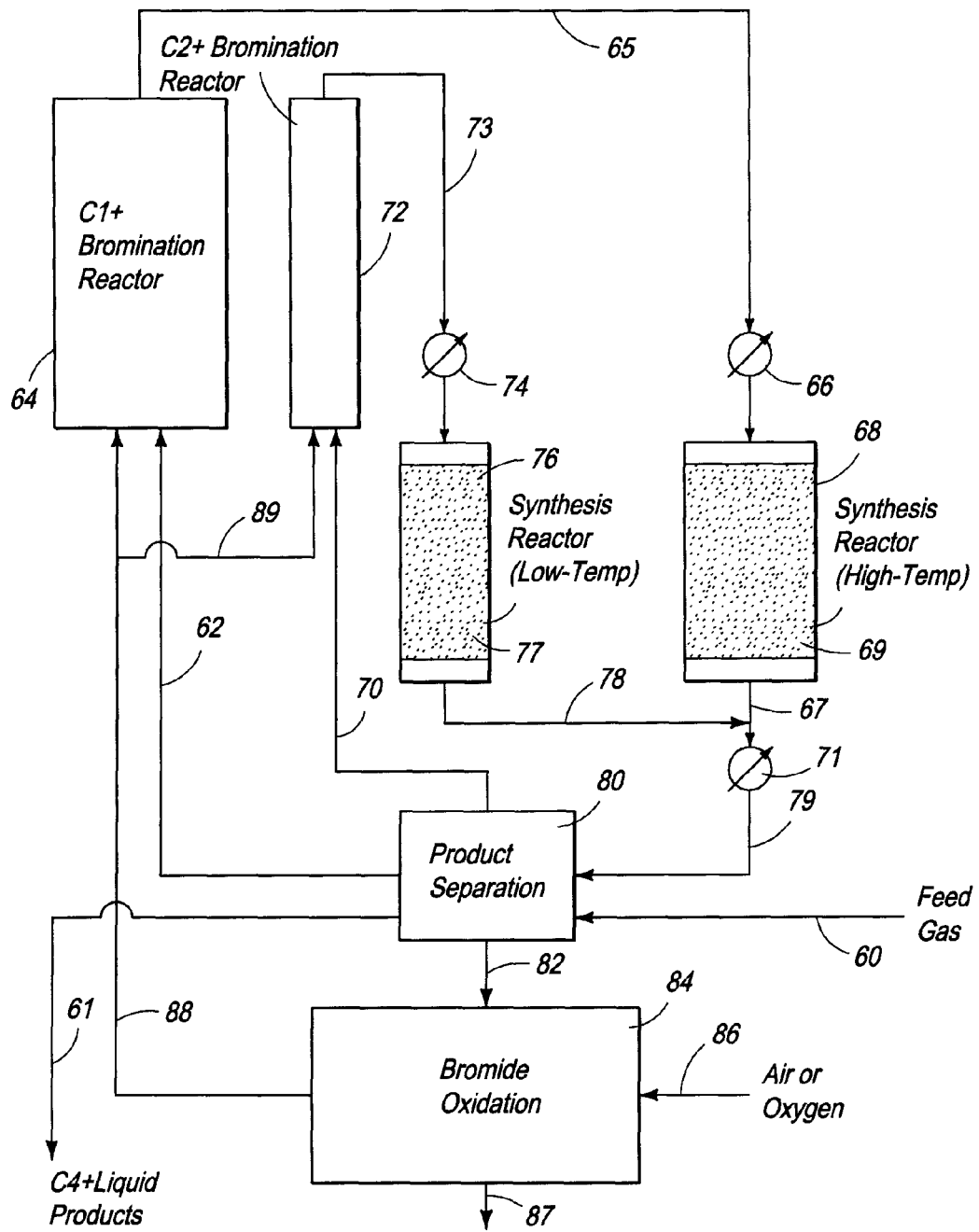
FIG. 5 is a schematic view of yet another embodiment of the processes and systems of the present invention.

A block flow diagram generally depicting some aspects of certain embodiments of the processes and systems of the present invention is illustrated in FIG. 5. A feed gas stream 60 containing lower molecular weight alkanes may be pretreated to remove $C_{2+}$ components prior to being combined with bromine vapor and conveyed to at least one $C_{1+}$ bromination reactor 64. The concentration of $C_{2+}$ components in the feed gas stream introduction into the $C_{1+}$ bromination reactor 64 may be from about 0.1 mol % to about 10.0 mol %, more preferably from about 0.1 mol % to about 1.0 mol %, and most preferably from about 0.1 mol % to about 0.5 mol %. While some $C_{2+}$ hydrocarbons may be tolerated in the $C_{1+}$ bromination reactor 64 in the embodiment of FIG. 5, higher concentrations than set forth above may result in the rapid formation of carbon-containing coke-like solids which cause fouling and plugging in the bromination reactor as well as downstream components. The feed gas to the processes and systems illustrated in FIG. 5 may be combined with the effluent 79 from the synthesis reactors 76 and 68 and pretreated in a product separation stage to selectively remove $C_{2+}$ components and product hydrocarbons. More specifically, the feed gas, residual hydrocarbons and product hydrocarbons, e.g. high molecular weight hydrocarbons, olefins or mixtures thereof, may be conveyed to a product separation unit 80. The high molecular weight hydrocarbons, olefins or mixtures thereof as well as $C_{2+}$ components may be then separated from the feed gas resulting in a $C_{1+}$ hydrocarbon stream 62 which is primarily methane with acceptable concentrations of $C_{2+}$ lower molecular alkane components as described above. The $C_{2+}$ components may also be separated from the product hydrocarbons in the product separation unit 80 and used in conjunction with a $C_{2+}$ bromination reactor in a manner as hereinafter described, while the liquid hydrocarbon product may be removed as stream 61 from a product stabilizer column (not illustrated) in the product separation unit 80 for use or further petrochemical or fuel processing.

The $C_{1+}$ stream 62 may be combined with a bromine stream 88 prior to, upon introduction into or within at least one $C_{1+}$ bromination reactor 64. The ratio of methane to bromine that may be utilized in the feed to the $C_{1+}$ bromination reactor is a function of the $C_{2+}$ content of the $C_{1+}$ stream as well as the temperature. Lower $C_{2+}$ content in the $C_{1+}$ stream and operation at lower temperatures may allow operation at lower methane to bromine ratios.

Hence with the appropriate control of the $C_{2+}$ content of the $C_{1+}$ stream, the molar ratio of methane to bromine in the feed to the $C_{1+}$ bromination reactor 64 is less than about 7 to 1 but greater than about 1.25 to 1, and preferably less than about 4 to 1 but greater than about 2 to 1, and more preferably less than or equal to about 3 to 1 but greater than about 2.5 to 1. The $C_{1+}$ stream 62 and a liquid bromine stream 88 may be mixed and conveyed to a heat exchanger (not illustrated) wherein the mixture is heated to a temperature between about 300° C. to about 550° C., but more preferably in the range of about 450° C. to about 500° C., and wherein the liquid bromine is vaporized and the bromination reaction is initiated.

Further, in some embodiments, the dry bromine vapor in the mixture fed into the $C_{1+}$ bromination reactor may be substantially water-free. Applicant has discovered that, at least in some instances, this may be preferred because it appears that elimination of substantially all water vapor from the bromination step substantially eliminates the formation of unwanted carbon dioxide. This may increase the selectivity of alkane bromination to alkyl bromides, thus possibly eliminating the large amount of waste heat generated in the formation of carbon dioxide from alkanes.

The heated mixture, containing predominantly methane, acceptable amounts of $C_{2+}$ lower molecular weight alkane components, and bromine vapor, may be introduced to a $C_{1+}$ bromination reactor 64 wherein lower molecular weight alkanes, predominantly methane and an acceptable amount of $C_{2+}$ lower molecular weight alkanes, present in the mixture are thermally brominated. If necessary, the $C_{1+}$ bromination reactor 64 may contain an inlet pre-heater zone (not illustrated) to ensure that the mixture remains heated to a reaction initiation temperature in the range of about 300° C. to about 550° C. In the case of methane, the formation of methyl bromide is believed to occur in accordance with the following general reaction:

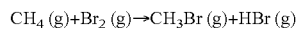

$$CH_4(g) + Br_2(g) \rightarrow CH_3Br(g) + HBr(g)$$

Where substantially all of the elemental bromine has been reacted away, the effluent stream 65 from the $C_{1+}$ bromination reactor 64 is a mixture of alkyl bromides and hydrogen bromide and unreacted lower molecular weight alkanes, predominately methane. The effluent stream 65 may be removed from the $C_{1+}$ bromination reactor 64 and introduced directly into a high temperature synthesis reactor 68. The $C_{1+}$ bromination reactor 64 may also contain a catalytic shift zone. The temperature of this feed to the catalytic shift zone may be in the range of about 350° C. to about 570° C., more preferably 500° C. to about 570° C., and most preferably 530° C. to about 570° C. As the $C_{1+}$ thermal bromination reaction is exothermic, the feed gas and bromine introduced to the $C_{1+}$ bromination reactor may be heated to a temperature within the about 300° C. to about 550° C. range to ensure that the effluent from the thermal bromination zone of the $C_{1+}$ bromination reactor 64 is within the desired range for introduction into the catalytic shift zone given the reactor operating conditions of the thermal bromination reactor as will be evident to a skilled artisan. Alternatively, the effluent mixture from the thermal bromination zone or reactor may be heated or cooled to a temperature within the range of about 350° C. to about 570° C. prior to contact with the catalyst employed in the catalytic shift zone by any suitable means (not illustrated) as evident to a skilled artisan.

The catalyst useful in the catalytic shift zone of the C1+ bromination reactor in the embodiment of the processes of the present invention illustrated generally in FIG. 5 may be a metallic element that is capable of forming both metal halides or metal oxy-halides, or mixtures thereof, and include Fe, Mo, La, Ce, W, Cr, Co, Ni, Cu, Ag, Zn, Mn, V, Nb, Ta, Ti, Y, Zr, Mg and Ca. Halogens that may be useful for the formation of catalytically-active metal halides or metal oxy-halides are Br, Cl and F, with Br being preferred.

While the catalyst may be initially prepared as a metal bromide dispersed on a catalyst support, it is generally more common to disperse a metal oxide by an incipient wetness technique utilizing a metal nitrate solution precursor, followed by drying and calcination at high-temperature in air or other oxidizing gas mixture. Further, as many metal bromide salts are hygroscopic, handling, storage and transport may require special measures. Accordingly the catalyst used in the catalytic shift zone may be most practically, commercially available in only the metal oxide state. Such a metal oxide catalyst may be initially employed in the catalytic shift zone within reactor 64 of FIG. 5 as it will be converted into a metal bromide or metal oxy-bromide, or mixtures thereof over time due to the reaction thereof with hydrogen bromide, methyl bromide, di-bromomethane or other alkyl bromides. However, as activity of a metal oxide catalyst in the catalytic shift zone is appreciably less than that of a metal bromide or metal oxy-bromide and carbon losses or coking is increased until conversion is completed, it may be desirable to convert the initial metal oxide catalyst in-situ to a metal bromide or metal oxy-bromide, or mixtures thereof prior to introduction of feed into the catalytic shift zone or reactor by any suitable means, such as by reaction with hydrogen bromide and a carrier gas, for example methane or nitrogen.

In the catalytic shift zone, a significant portion of the di- and tri- brominated alkanes that may be present in the alkyl bromides contained in the effluent from the thermal bromination zone may be selectively converted upon reaction with the unreacted alkane components, predominantly methane, present in the feed, to mono-brominated alkanes. As an example, where C1 and di-bromomethane are the reactants, it is believed that the conversion occurs in accordance with the following general reaction:

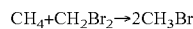

$$CH_4 + CH_2Br_2 \rightarrow 2CH_3Br$$

Due to the high temperatures in the both the thermal and catalytic zones, elemental bromine is likely to be essentially completely converted. It is believed that the catalyst used in the catalytic shift zone or reactor promotes a selective reaction of di-bromomethane with methane to yield methyl bromide via a selective catalytic reaction of bromine (supplied by dissociative adsorption of di-bromomethane on the catalyst surface) with methane. The effluent from the catalytic shift zone of the $C_{1+}$ bromination reactor which contains a significantly increased ratio of mono-brominated alkanes to di- or tri-brominated alkanes may then be transported to a high temperature synthesis reactor 68. While the thermal and catalytic shift zones have been described above as contained within a single $C_{1+}$ bromination reactor 64, these zones can each be contained in at least two separate reactors arranged in series as will be evident to a skilled artisan.

The effluent stream 65 from the $C_{1+}$ bromination reactor may be cooled or heated by any suitable means, such as a heat exchanger 66, before being introduced into a high temperature synthesis reactor 68. In the high temperature synthesis reactor, the methyl and ethyl bromides may be reacted exothermically at a temperature in the range of about 300° C. to about 450° C., and more preferably in the range of about 350° C. to about 425° C., and at a pressure in the range of about 1 to about 100 bar, over a suitable catalyst to produce a stream 67 of desired hydrocarbon products (e.g., high molecular weight hydrocarbons, olefins or mixtures thereof). It is believed that at these conditions the methyl bromides and ethyl bromides are reactive over a suitable catalyst to preferentially oligomerize the methyl and ethyl units thereby forming hydrocarbon products, for example high molecular weight hydrocarbons, olefins or mixtures thereof, that contain $C_{7+}$ fractions having primarily substituted aromatics and also light alkanes primarily in the $C_3$ to $C_{5+}$ range.

A stream 70 of $C_{2+}$ components may be produced by the process or contained in the feed gas which are removed in the product separation unit 80 so that the feed to the $C_{1+}$ thermal bromination contains an acceptable amount of $C_{2+}$. The excess $C_{2+}$ and in particular $C_{3+}$ may be separately processed in a $C_{2+}$ thermal bromination reactor 72 using a slip stream 89 of the liquid bromine feed. The $C_{2+}$ thermal bromination reactor 72 operates at an alkane to bromine ratio of in the range of about 4 to 1 to about 1.25 to 1, and preferably in the range of about 2 to 1 to about 1.5 to 1 and at a temperature in the range of about 250° C. to 550° C.

The effluent 73 from the $C_{2+}$ thermal bromination reactor contains various alkyl bromides and hydrogen bromide may be cooled or heated by any suitable means, such as a heat exchanger 74, to about 150° C. to about 300° C., more preferably from about 225° C. to about 275° C., before being introduced into to a low temperature synthesis reactor 76. In the low temperature synthesis reactor, the alkyl bromides may be reacted exothermically at a temperature range of from about 150° C. to about 300° C., and more preferably from about 225° C. to about 275° C., and at a pressure in the range of about 1 to about 100 bar, over a suitable catalyst 77 to produce desired hydrocarbons products (e.g., high molecular weight hydrocarbons, olefins or mixtures thereof). It is believed that at these conditions propyl bromide is more reactive than methyl bromide or ethyl bromide over a suitable catalyst thereby preferentially oligomerizing the propyl units thereby forming hydrocarbons products, for example high molecular weight hydrocarbons, olefins or mixtures thereof, that contain a substantial $C_{6+}$ paraffin content and thus a reduced aromatic content. In the first stage synthesis reactor, only a portion of the mono-brominated alkanes present in the alkyl bromides may be converted, and any poly-brominated alkanes which may be present may have a lower propensity to be converted to heavy products or "coke" which deposit on the catalyst, due to the presence of propyl bromide and the lower temperature conditions.

The catalyst 77 and 69 employed in the low temperature and high temperature synthesis reactors 76 and 68, respectively, may be any of a variety of suitable materials for catalyzing the conversion of the alkyl bromides to product hydrocarbons as previously set forth. In certain embodiments, the low temperature and high temperature synthesis reactors may comprise a fixed bed of the catalyst. A fluidized-bed of synthesis catalyst may also be used in certain circumstances, particularly in larger applications and may have certain advantages, such as constant removal of coke and a steady selectivity to product composition. The particular catalyst used in both the low temperature and high temperature synthesis reactors will depend, for example, upon the particular product hydrocarbons that are desired. For example, when product hydrocarbons having primarily $C_3$, $C_4$ and $C_{5+}$ gasoline-range paraffinic compounds and heavier hydrocarbon fractions are desired, a ZSM-5 zeolite catalyst may be used. When it is desired to produce product hydrocarbons comprising a mixture of olefins and $C_{5+}$ products, an X-type or Y-type zeolite catalyst or SAPO zeolite catalyst may be used. Examples of suitable zeolites include an X-type, such as 10-X, or Y-type zeolite, although other zeolites with differing pore sizes and acidities, may be used in embodiments of the present invention. The catalyst used in the low temperature and high temperature synthesis reactors need not be identical so long as the catalyst used in both reactors are selected to form the similar products, e.g. selected to form hydrocarbons having primarily $C_3$, $C_4$ and $C_{5+}$ gasoline-range paraffinic compounds and heavier hydrocarbon fractions.

The effluent streams 78 and 67 from the low temperature and the high temperature synthesis reactors 76 and 68, respectively, may be combined into one synthesis effluent stream 79 and cooled by suitable means such as heat exchanger 71 to recover heat for use elsewhere in the process, such as to produce steam or preheat feed to the process (not shown) or for other uses as determined by the skilled artisan, and then conveyed to a product separation stage 80. Hydrogen bromide may be removed from the hydrocarbon product, e.g. high molecular weight hydrocarbons, olefins or mixtures thereof, and a stream 82 of hydrogen bromide may be conveyed to a bromide oxidation stage 84 wherein hydrogen bromide may be neutralized by a partially oxidized metal bromide salt to yield a metal bromide salt and steam. A stream 86 of oxygen or air may be introduced to the bromide oxidation stage 84 to contact the resultant metal bromide so as to yield elemental bromine. A stream 88 of bromine may be recycled to the bromination stage as a dry bromine vapor and a partially oxidized metal bromide salt which may be used to neutralize and remove additional hydrogen bromide from the hydrocarbons produced by the process. The steam produced from the oxidation of the HBr with partially oxidized metal bromide salt may be condensed, stripped of any residual bromine, and removed as a byproduct liquid water product 87.

Figure 6:
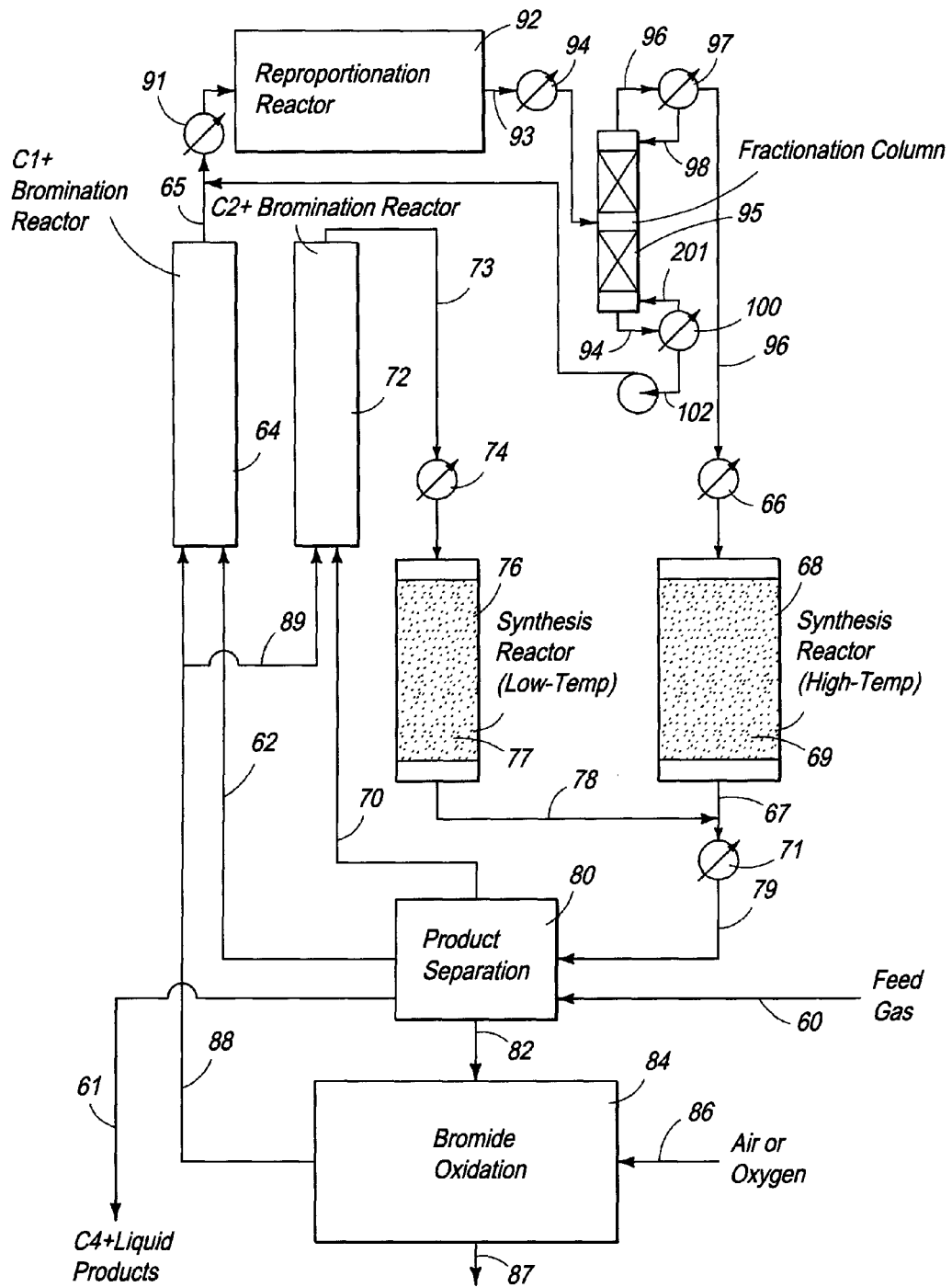
FIG. 6 is a schematic view of still another embodiment of the processes and systems of the present invention.

A block flow diagram generally depicting some aspects of certain embodiments of the processes and systems of the present invention is illustrated in FIG. 6 and is similar to that illustrated in FIG. 5 and described above except that effluent from the $C1_+$ bromination reactor is combined with recycled poly-bromides, heated and thermally reacted so as to convert poly-brominated alkanes present in the alkyl bromide stream to mono-brominated alkanes prior to introduction into the high temperature synthesis reactor 68. As illustrated in FIG. 6, the effluent stream 65 from the $C_{1+}$ bromination reactor, which is a mixture of alkyl bromides and hydrogen bromide, may be combined with recycled poly-bromides and the mixture subsequently heated to a temperature of from about 450° C. to about 570° C. by any suitable means, such as heat exchanger, and transported to reproportionation reactor 92 wherein at least a portion of the poly-brominated alkanes present in the effluent stream are converted to mono-brominated alkanes. Reproportionation reactor 92 may be a relatively long, open-ended tube to allow sufficient residence time, preferably in the range of approximately 15 to 60 seconds to permit conversion of at least a portion of the poly-brominated alkanes present in the effluent stream to mono-brominated alkanes. The effluent stream 93 from the reproportionation reactor 92 may then be cooled by any suitable means, such as heat exchanger 94, and introduced into a fractionation column 95 wherein poly-brominated alkanes, e.g. bi- and tri-brominated alkanes, are removed from the effluent. The fractionation column bottom liquid stream 99 which contains such poly-brominated alkanes may be passed to the fractionator reboiler 100 which vaporizes a fraction of the liquid, stripping the residual lighter mono-brominated alkanes from the heavier poly-brominated alkanes in the liquid. The residual light mono-brominated alkanes may be recycled to the fractionator 95 as stream 101. Stream 102 containing poly-brominated alkanes may be combined with effluent stream 65 from the $C_{1+}$ bromination reactor and preheated to a temperature of about 450° C. to about 570° C. prior to introduction into reproportionation reactor 92 wherein the poly-brominated alkanes are reacted with $C_{1+}$ to further form predominately mono-brominated alkanes. The fractionator overhead vapor stream 96 which been separated from the poly-brominated alkanes in the fractionation column may be conveyed to a condenser 97 wherein any remaining poly-brominated alkanes may be condensed and refluxed as stream 98 to the fractionation column 95. The remaining stream 96 comprising predominately alkyl bromides and hydrogen bromide may be heated by any suitable means, such as a heat exchanger 66, before being introduced into a high temperature synthesis reactor 68 in accordance with the embodiments of the processes and systems of the present invention illustrated in FIGS. 4 and 5 described above in detail. The remaining streams and process equipment illustrated in FIG. 6 are operated in accordance with the embodiments of the processes and systems of the present invention illustrated in FIG. 5 and described above in detail.

Where a feed gas contains a substantial amount of gases suitable for use as liquefied petroleum gas (LPG), such LPG may be separated from the feed gas for use as an end product or as an intermediate feedstock for another process. Alternatively, it may be desirable to convert such LPG to product hydrocarbons, for example $C5_+$ gasoline-range paraffinic compounds and heavier hydrocarbon fractions, which may have greater value and use. The block flow diagrams generally depicting some aspects of certain embodiments of the present invention illustrated in FIGS. 5 and 6 and described above provide processes and systems for converting $C3_+$ components of a feed gas, i.e. LPG components to product hydrocarbons.

While the foregoing preferred embodiments of the invention have been described and shown, it is understood that the alternatives and modifications, such as those suggested and others, may be made thereto and fall within the scope of the invention.

We claim:

1. A process comprising:
providing alkyl bromides;
reacting at least a first portion of the alkyl bromides in the presence of a first catalyst and at a first temperature sufficient to form a first hydrocarbon product containing at least hydrocarbons having at least 5 carbon atoms and having a substantial $C_{6+}$ paraffin content; and
reacting at least a second portion of the alkyl bromides in the presence of a second catalyst and said first hydrocarbon product and at a second temperature sufficient to form a second hydrocarbon product containing at least hydrocarbons having at least 5 carbon atoms and having a substantial substituted aromatic content, wherein the steps of reacting at least the first portion of the alkyl bromides and reacting at least the second portion of the alkyl bromides occur sequentially.

2. The process of claim 1 wherein said first temperature is from about 150° C. to about 300° C.

3. The process of claim 2 wherein said first temperature is from about 225° C. to about 275° C.

4. The process of claim 1 wherein said second temperature is from about 300° C. to about 450° C.

5. The process of claim 4 wherein said second temperature is from about 350° C. to about 425° C.

6. The process of claim 1 wherein the steps of reacting at least the first portion of the alkyl bromides and reacting at least the second portion of the alkyl bromides occurs concurrently.

7. The process of claim 1 wherein the first catalyst and the second catalyst are identical.

8. The process of claim 1 wherein the first catalyst is a crystalline alumino-silicate catalyst.

9. The process of claim 8 wherein said first catalyst is a zeolite catalyst.

10. The process of claim 1 wherein the second catalyst is a crystalline alumino-silicate catalyst.

11. The process of claim 10 wherein said second catalyst is a zeolite catalyst.

12. The process of claim 1 wherein said first temperature is from about 150° C. to about 300° C. and said second temperature is from about 300° C. to about 450° C.

13. The process of claim 1 further comprising:
combining said first hydrocarbon product and said second hydrocarbon product.

14. The process of claim 13 further comprising:
removing hydrogen bromide from said first hydrocarbon product and said second hydrocarbon product.

15. The process of claim 1 wherein the first catalyst and the second catalyst are different.

16. The process of claim 1 wherein the steps of reacting at least the first portion of the alkyl bromides and reacting at least the second portion of the alkyl bromides occurs in separate reactors.

17. The process of claim 1 further comprising:
heating at least the second portion of the alkyl bromides prior to reacting at least the second portion of the alkyl bromides in the presence of the second catalyst and the first hydrocarbon product.

18. The process of claim 1 wherein the step of reacting at least the first portion of the alkyl bromides is performed at a pressure in the range of about 1 to about 100 bar.

19. The process of claim 1 wherein the step of reacting at least the second portion of the alkyl bromides is performed at a pressure in the range of about 1 to about 100 bar.

* * * * *